(12) United States Patent
Stein

(10) Patent No.: US 9,125,627 B2
(45) Date of Patent: Sep. 8, 2015

(54) WIRELESS POWER MODULATION TELEMETRY FOR MEASURING A PARAMETER OF THE MUSCULAR-SKELETAL SYSTEM

(75) Inventor: Marc Stein, Chandler, AZ (US)

(73) Assignee: ORTHOSENSOR INC., Dania Beach, FL (US)

(*) Notice: Subject to any disclaimer, the term of this patent is extended or adjusted under 35 U.S.C. 154(b) by 446 days.

(21) Appl. No.: 12/825,716

(22) Filed: Jun. 29, 2010

(65) Prior Publication Data

US 2010/0328077 A1 Dec. 30, 2010

Related U.S. Application Data

(60) Provisional application No. 61/221,761, filed on Jun. 30, 2009, provisional application No. 61/221,767, filed on Jun. 30, 2009, provisional application No. 61/221,779, filed on Jun. 30, 2009, provisional (Continued)

(51) Int. Cl.
*A61B 5/00* (2006.01)
*A61B 8/15* (2006.01)

(52) U.S. Cl.
CPC ............ *A61B 5/6878* (2013.01); *A61B 5/4528* (2013.01); *A61B 5/6846* (2013.01); *A61B 8/15* (2013.01); *A61B 5/4509* (2013.01); *A61B 5/7239* (2013.01); *Y10T 307/615* (2013.01)

(58) Field of Classification Search
USPC ................. 340/573.1, 539.12, 539.3, 538.15, 340/538.16, 538.17, 539.11, 539.19, 340/539.21, 539.23, 539.24; 600/587, 382; 623/18.11, 18.12
See application file for complete search history.

(56) References Cited

U.S. PATENT DOCUMENTS

| | | | | |
|---|---|---|---|---|
| 3,495,149 A | * | 2/1970 | Swain | 318/400.27 |
| 4,327,422 A | * | 4/1982 | Imazeki et al. | 365/1 |
| 4,453,162 A | * | 6/1984 | Money et al. | 340/870.39 |
| 4,462,113 A | * | 7/1984 | Iwata | 455/20 |
| 5,197,488 A | | 3/1993 | Kovacevic | |
| 5,335,664 A | * | 8/1994 | Nagashima | 600/508 |
| 5,470,354 A | | 11/1995 | Hershberger et al. | |
| 5,683,396 A | | 11/1997 | Tokish et al. | |
| 5,686,882 A | * | 11/1997 | Giani | 340/407.1 |
| 5,688,279 A | | 11/1997 | McNulty et al. | |
| 5,871,018 A | | 2/1999 | Delp et al. | |
| 6,171,252 B1 | | 1/2001 | Roberts | |

(Continued)

FOREIGN PATENT DOCUMENTS

WO WO 0145561 A1 * 6/2001

*Primary Examiner* — Paul Obiniyi

(57) ABSTRACT

A sensing insert device (100) is disclosed for measuring a parameter of the muscular-skeletal system. The sensing insert device (100) can be temporary or permanent. Used intra-operatively, the sensing insert device (100) comprises an insert dock 202 and a sensing module 200. The sensing module (200) is a self-contained encapsulated measurement device having at least one contacting surface that couples to the muscular-skeletal system. The sensing module (200) comprises one or more sensors (303), electronic circuitry (307), and communication circuitry (320). The electronic circuitry (307) operatively couples to the one or more sensors (303) to measure the parameter. A transmitter (309) transmits parameter measurements. An induction coil (1404) is coupled electromagnetically to a wireless energy source (1402). The induction coil converts electromagnetic energy waves to a signal that powers the sensing module (200). The signal includes information or data. The signal is demodulated to capture the data or information.

13 Claims, 9 Drawing Sheets

Related U.S. Application Data application No. 61/221,788, filed on Jun. 30, 2009, provisional application No. 61/221,793, filed on Jun. 30, 2009, provisional application No. 61/221,801, filed on Jun. 30, 2009, provisional application No. 61/221,808, filed on Jun. 30, 2009, provisional application No. 61/221,817, filed on Jun. 30, 2009, provisional application No. 61/221,867, filed on Jun. 30, 2009, provisional application No. 61/221,874, filed on Jun. 30, 2009, provisional application No. 61/221,879, filed on Jun. 30, 2009, provisional application No. 61/221,881, filed on Jun. 30, 2009, provisional application No. 61/221,886, filed on Jun. 30, 2009, provisional application No. 61/221,889, filed on Jun. 30, 2009, provisional application No. 61/221,894, filed on Jun. 30, 2009, provisional application No. 61/221,901, filed on Jun. 30, 2009, provisional application No. 61/221,909, filed on Jun. 30, 2009, provisional application No. 61/221,916, filed on Jun. 30, 2009, provisional application No. 61/221,923, filed on Jun. 30, 2009, provisional application No. 61/221,929, filed on Jun. 30, 2009.

(56) References Cited

U.S. PATENT DOCUMENTS

| | | | | |
|---|---|---|---|---|
| 6,245,109 | B1 | 6/2001 | Mendes et al. | |
| 6,583,630 | B2 * | 6/2003 | Mendes et al. | 324/652 |
| 6,621,278 | B2 | 9/2003 | Ariav | |
| 6,685,654 | B2 * | 2/2004 | Yoshimura et al. | 600/587 |
| 6,701,174 | B1 | 3/2004 | Krause et al. | |
| 6,714,763 | B2 | 3/2004 | Hamel et al. | |
| 6,821,299 | B2 | 11/2004 | Kirking et al. | |
| 6,856,141 | B2 | 2/2005 | Ariav | |
| 7,001,346 | B2 | 2/2006 | White | |
| 7,097,662 | B2 | 8/2006 | Evans et al. | |
| 7,164,344 | B2 * | 1/2007 | Deguchi et al. | 340/10.51 |
| 7,195,645 | B2 * | 3/2007 | Disilvestro et al. | 623/18.11 |
| 7,245,211 | B2 * | 7/2007 | Ota | 340/505 |
| 7,256,695 | B2 | 8/2007 | Hamel et al. | |
| 7,295,724 | B2 | 11/2007 | Wang et al. | |
| 7,308,614 | B2 * | 12/2007 | Kojori | 714/47.2 |
| 7,442,196 | B2 | 10/2008 | Fisher et al. | |
| 7,492,250 | B2 * | 2/2009 | Yoshida et al. | 340/539.19 |
| 7,575,602 | B2 | 8/2009 | Amirouche et al. | |
| 7,578,821 | B2 | 8/2009 | Fisher et al. | |
| 7,583,930 | B2 * | 9/2009 | Minotani et al. | 455/41.1 |
| 7,587,945 | B2 | 9/2009 | Crottet et al. | |
| 7,615,055 | B2 | 11/2009 | DiSilvestro | |
| 7,632,283 | B2 | 12/2009 | Heldreth | |
| 7,782,192 | B2 * | 8/2010 | Jeckelmann et al. | 340/539.12 |
| 8,077,601 | B2 * | 12/2011 | Maze et al. | 370/216 |
| 2001/0053883 | A1 * | 12/2001 | Yoshimura et al. | 600/587 |
| 2002/0029784 | A1 | 3/2002 | Stark et al. | |
| 2002/0105427 | A1 * | 8/2002 | Hamamoto et al. | 340/576 |
| 2003/0080868 | A1 | 5/2003 | Nelson | 340/551 |
| 2004/0066278 | A1 * | 4/2004 | Hughes et al. | 340/10.1 |
| 2004/0066279 | A1 * | 4/2004 | Hughes et al. | 340/10.1 |
| 2005/0020941 | A1 | 1/2005 | Tarabichi | |
| 2006/0058798 | A1 | 3/2006 | Roman et al. | |
| 2006/0149167 | A1 * | 7/2006 | Yeh et al. | 600/587 |
| 2006/0232408 | A1 | 10/2006 | Nyez et al. | |
| 2006/0271112 | A1 | 11/2006 | Martinson et al. | |
| 2006/0271199 | A1 * | 11/2006 | Johnson | 623/18.12 |
| 2007/0219561 | A1 | 9/2007 | Lavallee et al. | |
| 2007/0272747 | A1 | 11/2007 | Woods et al. | |
| 2008/0061964 | A1 * | 3/2008 | Yoshida et al. | 340/539.19 |
| 2008/0129486 | A1 * | 6/2008 | Jeckelmann et al. | 340/539.12 |
| 2009/0177109 | A1 * | 7/2009 | Yeh et al. | 600/546 |
| 2010/0097830 | A1 * | 4/2010 | Wang | 363/126 |
| 2010/0191055 | A1 * | 7/2010 | Minai et al. | 600/109 |
| 2010/0320973 | A1 * | 12/2010 | Nishida | 320/145 |

* cited by examiner

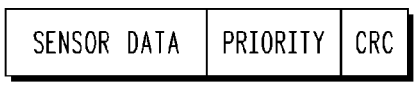
DATA PACKET
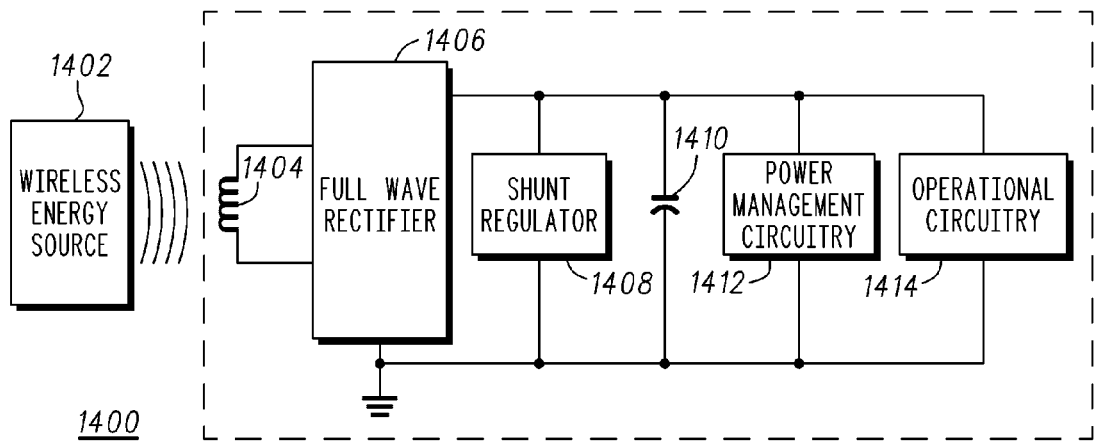
*Fig. 13*
*Fig. 14*
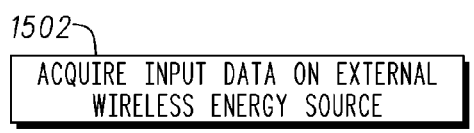
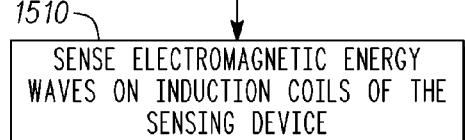
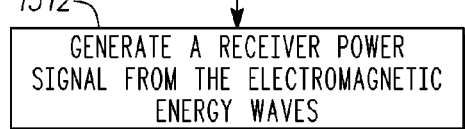
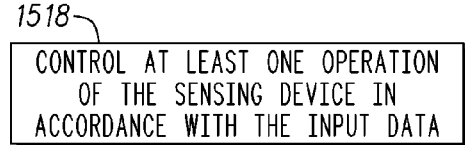
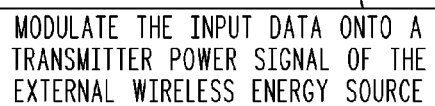
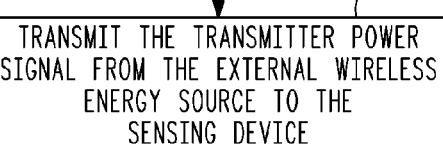
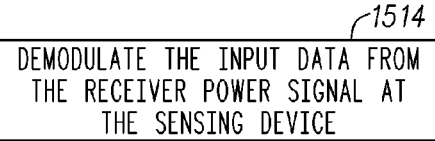
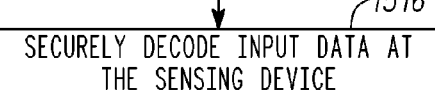
*Fig. 15*

WIRELESS POWER MODULATION TELEMETRY FOR MEASURING A PARAMETER OF THE MUSCULAR-SKELETAL SYSTEM

CROSS-REFERENCE TO RELATED APPLICATIONS

This application claims the priority benefit of U.S. provisional patent applications Nos. 61/221,761, 61/221,767, 61/221,779, 61/221,788, 61/221,793, 61/221,801, 61/221,808, 61/221,817, 61/221,867, 61/221,874, 61/221,879, 61/221,881, 61/221,886, 61/221,889, 61/221,894, 61/221,901, 61/221,909, 61/221,916, 61/221,923, and 61/221,929 all filed 30 Jun. 2009; the disclosures of which are hereby incorporated herein by reference in their entirety.

FIELD

The present relates generally to the communication of data, and more particularly, but not exclusively, to secure communication of data and measurements in real-time.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

Various features of the system are set forth with particularity in the appended claims. The embodiments herein, can be understood by reference to the following description, taken in conjunction with the accompanying drawings, in which:

FIG. 13 is an illustration of an exemplary data packet containing sensor data;

FIG. 14 is an exemplary block diagram schematic of a compact low-power energy source integrated into an exemplary electronic assembly of the sensing module in accordance with one embodiment; and FIG. 15 is an exemplary flow chart of a method for wireless power modulation telemetry in accordance with one embodiment.

DETAILED DESCRIPTION

Figure 1:
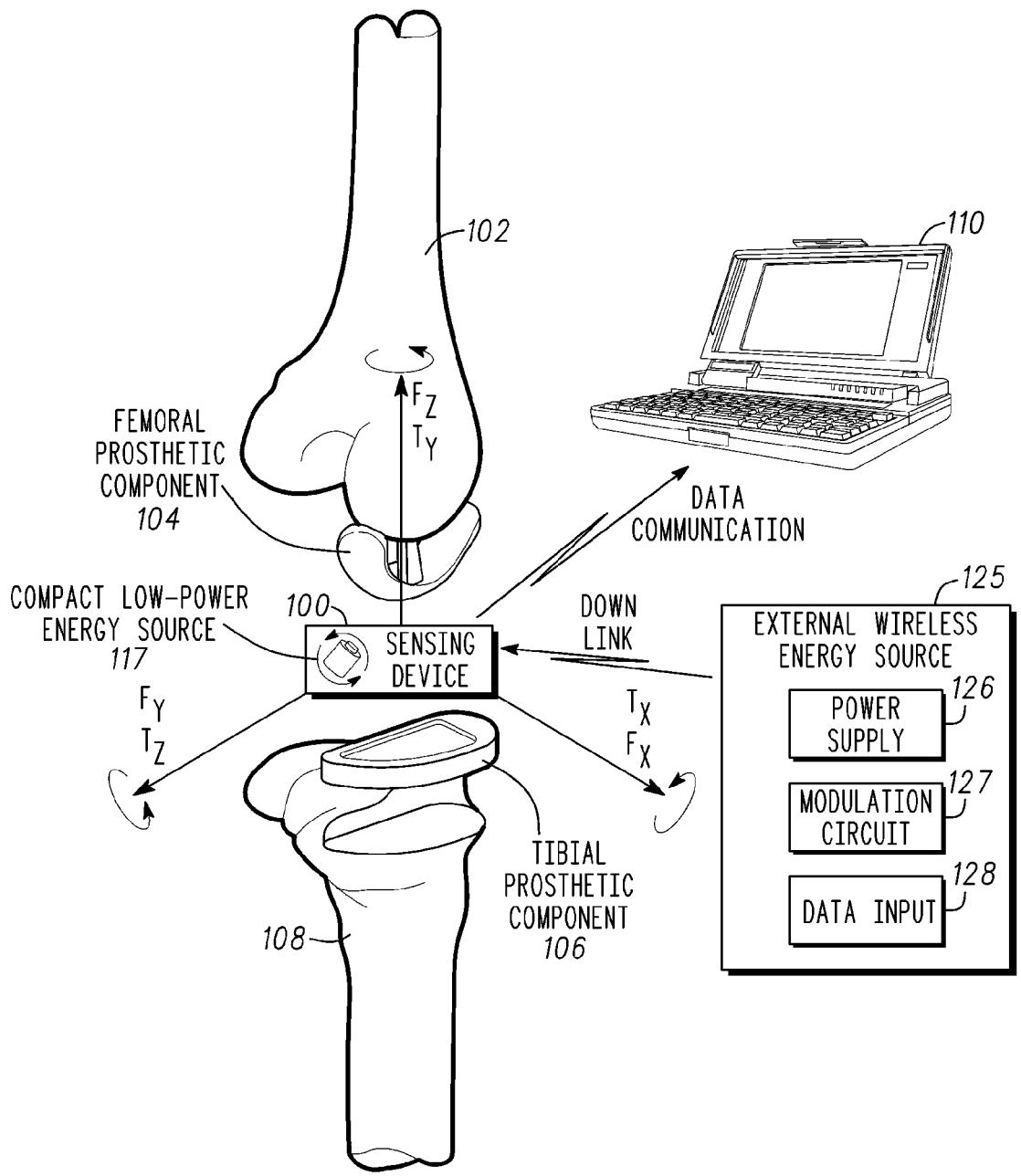
FIG. 1 is an illustration of an application of sensing insert device in accordance with an exemplary embodiment.

Embodiments of the invention are broadly directed to measurement of physical parameters. Many physical parameters of interest within physical systems or bodies can be measured by evaluating changes in the characteristics of energy waves or pulses. As one example, changes in the transit time or shape of an energy wave or pulse propagating through a changing medium can be measured to determine the forces acting on the medium and causing the changes. The propagation velocity of the energy waves or pulses in the medium is affected by physical changes in of the medium. The physical parameter or parameters of interest can include, but are not limited to, measurement of load, force, pressure, displacement, density, viscosity, localized temperature. These parameters can be evaluated by measuring changes in the propagation time of energy pulses or waves relative to orientation, alignment, direction, or position as well as movement, rotation, or acceleration along an axis or combination of axes by wireless sensing modules or devices positioned on or within a body, instrument, appliance, vehicle, equipment, or other physical system.

In all of the examples illustrated and discussed herein, any specific materials, temperatures, times, energies, etc. for process steps or specific structure implementations should be interpreted to illustrative only and non-limiting. Processes, techniques, apparatus, and materials as known by one of ordinary skill in the art may not be discussed in detail but are intended to be part of an enabling description where appropriate.

Note that similar reference numerals and letters refer to similar items in the following figures. In some cases, numbers from prior illustrations will not be placed on subsequent figures for purposes of clarity. In general, it should be assumed that structures not identified in a figure are the same as previous prior figures.

In the present invention these parameters are measured with an integrated wireless sensing module or device comprising an i) encapsulating structure that supports sensors and contacting surfaces and ii) an electronic assemblage that integrates a power supply, sensing elements, ultrasound resonator or resonators or transducer or transducers and ultrasound waveguide or waveguides, biasing spring or springs or other form of elastic members, an accelerometer, antennas and electronic circuitry that processes measurement data as well as controls all operations of energy conversion, propagation, and detection and wireless communications. The wireless sensing module or device can be positioned on or within, or engaged with, or attached or affixed to or within, a wide range of physical systems including, but not limited to instruments, appliances, vehicles, equipments, or other physical systems as well as animal and human bodies, for sensing and communicating parameters of interest in real time.

FIG. 1 is an illustration of an application of sensing insert device 100 in accordance with an exemplary embodiment. The illustration shows the device 100 measuring a force, pressure, or load applied by the muscular-skeletal system. The sensing insert device 100 can measure the level and distribution of load at various points on the prosthetic component and transmits the measured load data by way secure short-range communication to a receiver for permitting visualization. This can aid the surgeon in making any adjustments needed to achieve optimal joint balancing.

In general, device 100 has at least one contacting surface that couples to the muscular-skeletal system. As shown, a first and a second contacting surface respectively couple to a femoral prosthetic component 104 and a tibial prosthetic component 106. Device 100 is designed to be used in the normal flow of an orthopedic surgical procedure without special procedures, equipment, or components. Typically, one or more natural components of the muscular-skeletal system are replaced when joint functionality substantially reduces a patient quality of life. A joint replacement is a common procedure in later life because it is prone to wear over time, can be damaged during physical activity, or by accident.

A joint of the muscular-skeletal system provides movement of bones in relation to one another that can comprise angular and rotational motion. The joint can be subjected to loading and torque throughout the range of motion. The joint typically comprises two bones that move in relation to one another with a low friction flexible connective tissue such as cartilage between the bones. The joint also generates a natural lubricant that works in conjunction with the cartilage to aid in ease of movement. Sensing insert device 100 mimics the natural structure between the bones of the joint. Insert device 100 has a contacting surface on which a bone or a prosthetic component can moveably couple. A knee joint is disclosed for illustrative purposes but sensing insert device 100 is applicable to other joints of the muscular-skeletal system. For example, the hip, spine, and shoulder have similar structures comprising two or more bones that move in relation to one another. In general, insert device 100 can be used between two or more bones allowing movement of the bones during measurement or maintaining the bones in a fixed position.

The load sensor insert device 100 and the receiver station 110 forms a communication system for conveying data via secure wireless transmission within a broadcasting range over short distances on the order of a few meters to protect against any form of unauthorized or accidental query. In one embodiment, the transmission range is five meters or less which is approximately a dimension of an operating room. In practice, it can be a shorter distance 1-2 meters to transmit to a display outside the sterile field. The transmit distance will be even shorter when device 100 is used in a prosthetic implanted component. Transmission occurs through the skin of the patient and is likely limited to less than 0.5 meters. A combination of cyclic redundancy checks and a high repetition rate of transmission during data capture permits discarding of corrupted data without materially affecting display of data In the illustration, a surgical procedure is performed to place a femoral prosthetic component 104 onto a prepared distal end of the femur 102. Similarly, a tibial prosthetic component 106 is placed to a prepared proximal end of the tibia 108. The tibial prosthetic component 106 can be a tray or plate affixed to a planarized proximal end of the tibia 108. The sensing insert device 100 is a third prosthetic component that is placed between the plate of the tibial prosthetic component 106 and the femoral prosthetic component 104. The three prosthetic components enable the prostheses to emulate the functioning of a natural knee joint. In one embodiment, sensing insert device 100 is used during surgery and replaced with a final insert after quantitative measurements are taken to ensure optimal fit, balance, and loading of the prosthesis.

In one embodiment, sensing insert device 100 is a mechanical replica of a final insert. In other words, sensing insert device 100 has substantially equal dimensions to the final insert. The substantially equal dimensions ensure that the final insert when placed in the reconstructed joint will have similar loading and balance as that measured by sensing insert device 100 during the trial phase of the surgery. Moreover, passive trial inserts are commonly used during surgery to determine the appropriate final insert. Thus, the procedure remains the same. It can measure loads at various points (or locations) on the femoral prosthetic component 104 and transmit the measured data to a receiving station 110 by way of an integrated loop antenna. The receiving station 110 can include data processing, storage, or display, or combination thereof and provide real time graphical representation of the level and distribution of the load.

As one example, the sensing insert device 100 can measure forces (Fx, Fy, and Fz) with corresponding locations and torques (e.g. Tx, Ty, and Tz) on the femoral prosthetic component 104 and the tibial prosthetic component 106. It can then transmit this data to the receiving station 110 to provide real-time visualization for assisting the surgeon in identifying any adjustments needed to achieve optimal joint balancing.

In a further example, an external wireless energy source 125 can be placed in proximity to the medical sensing device 100 to initiate a wireless power recharging operation. As an example, the external wireless energy source 125 generates energy transmissions that are wirelessly directed to the medical sensing device 100 and received as energy waves via resonant inductive coupling. The external wireless energy source 125 can modulate a power signal generating the energy transmissions to convey downlink data that is then demodulated from the energy waves at the medical sensing device 100. As described above, the sensing insert device 100 is a sensing insert device 100 suitable for use in knee joint replacement surgery. The external wireless energy source 125 can be used to power the sensing insert device 100 during the surgical procedure or thereafter when the surgery is complete and the sensing insert device 100 is implanted for long-term use. The method can also be used to provide power and communication where the sensing insert device 100 is in a final insert that is part of the final prosthesis implanted in the patient.

In one system embodiment, the sensing insert device 100 transmits measured parameter data to a receiver 110 via one-way data communication over the up-link channel for permitting visualization of the level and distribution of the parameter at various points on the prosthetic components. This, combined with cyclic redundancy check error checking, provides high security and protection against any form of unauthorized or accidental interference with a minimum of added circuitry and components. This can aid the surgeon in making any adjustments needed to optimize the installation. In addition to transmitting one-way data communications over the up-link channel to the receiver station 110, the sensing insert device 100 can receive downlink data from the external wireless energy source 125 during the wireless power recharging operation. The downlink data can include component information, such as a serial number, or control information, for controlling operation of the sensing insert device 100. This data can then be uploaded to the receiving system 110 upon request via the one-way up-link channel, in effect providing two-way data communications over separate channels.

Separating uplink and downlink telemetry eliminates the need for transmit-receive circuitry within the sensing insert device 100. Two unidirectional telemetry channels operating on different frequencies or with different forms of energy enables simultaneous up and downlink telemetry. Modulating energy emissions from the external wireless energy source 125 as a carrier for instructions achieves these benefits with a minimum of additional circuitry and components by leveraging existing circuitry and antenna, induction loop, or piezoelectric components on the load sensor insert device 100. The frequencies of operation of the up and downlink telemetry channels can also be selected and optimized to interface with other devices, instruments, or equipment as needed. Separating uplink and downlink telemetry also enables addition of downlink telemetry without altering or upgrading existing chip-set telemetry for the one-way transmit. That is, existing chip-set telemetry can be used for encoding and packaging data and error checking without modification, yet remain communicatively coupled to the separate wireless power down-link telemetry operation for download operations herein contemplated.

As shown, the wireless energy source 125 can include a power supply 126, a modulation circuit 127, and a data input 128. The power supply 126 can be a battery, a charging device, a capacitor, a power connection, or other energy source for generating wireless power signals to power the sensing insert device 100. The external wireless energy source can transmit energy in the form of, but not limited to, electromagnetic induction, or other electromagnetic or ultrasound emissions. In at least one exemplary embodiment, the wireless energy source 125 includes a coil to electromagnetically couple with an induction coil in sensing device 100 when placed in close proximity. The data input 128 can be a user interface component (e.g., keyboard, keypad, or touchscreen) that receives input information (e.g., serial number, control codes) to be downloaded to the load sensor insert device 100. The data input 128 can also be an interface or port to receive the input information from another data source, such as from a computer via a wired or wireless connection (e.g., USB, IEEE802.16, etc.). The modulation circuitry 127 can modulate the input information onto the power signals generated by the power supply 126.

Figure 2:
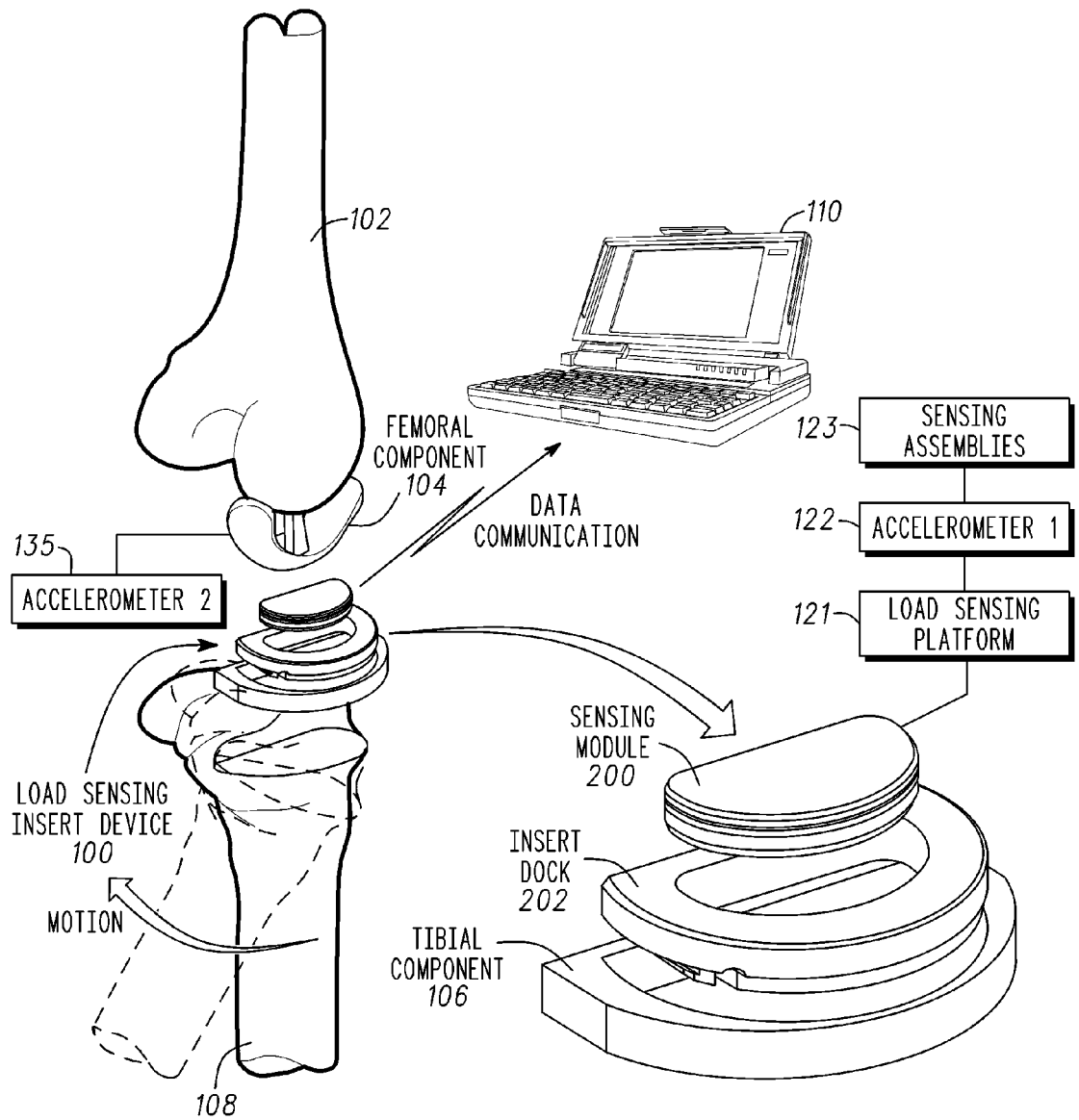
FIG. 2 is an illustration of a sensing insert device placed in a joint of the muscular-skeletal system for measuring a parameter in accordance with an exemplary embodiment.

FIG. 2 is an illustration of a sensing insert device 100 placed in a joint of the muscular-skeletal system for measuring a parameter in accordance with an exemplary embodiment. In particular, sensing insert device 100 is placed in contact between a femur 102 and a tibia 108 for measuring a parameter. In the example, a force, pressure, or load is being measured. The device 100 in this example can intra-operatively assess a load on prosthetic components during the surgical procedure. As mentioned previously, sensing insert device 100 collects data for real-time viewing of the load forces over various applied loads and angles of flexion. It can measure the level and distribution of load at various points on the prosthetic component and transmit the measured load data by way data communication to a receiver station 110 for permitting visualization. This can aid the surgeon in making any adjustments needed to achieve optimal joint balancing.

A proximal end of tibia 108 is prepared to receive tibial prosthetic component 106. Tibial prosthetic component 106 is a support structure that is fastened to the proximal end of the tibia and is usually made of a metal or metal alloy. The tibial prosthetic component 106 also retains the insert in a fixed position with respect to tibia 108. Similarly, a distal end of femur 102 is prepared to receive femoral prosthetic component 104. The femoral prosthetic component 104 is generally shaped to have an outer condylar articulating surface. The preparation of femur 102 and tibia 108 is aligned to the mechanical axis of the leg. The sensing insert device 100 provides a concave or flat surface against which the outer condylar articulating surface of the femoral prosthetic component 104 rides relative to the tibia prosthetic component 106. In particular, the top surface of the sensing module 200 faces the condylar articulating surface of the femoral prosthetic component 104, and the bottom surface of the insert dock 202 faces the top surface of the tibial prosthetic component 106.

A final insert is subsequently fitted between femoral prosthetic component 104 and tibial prosthetic component 106 that has a bearing surface that couples to femoral component 104 allowing the leg a natural range of motion. The final insert is has a wear surface that is typically made of a low friction polymer material. Ideally, the prosthesis has an appropriate loading, alignment, and balance that mimics the natural leg and maximizes the life of the artificial components. It should be noted that sensing module 200 can be placed a final insert and operated similarly as disclosed herein. The sensing module 200 can be used to periodically monitor status of the permanent joint.

The sensing insert device 100 is used to measure, adjust, and test the reconstructed joint prior to installing the final insert. As mentioned previously, the sensing insert device 100 is placed between the femur 102 and tibia 108. The condyle surface of femoral component 104 contacts a major surface of device 100. The major surface of device 100 approximates a surface of a final insert. Tibial prosthetic component 106 can include a cavity or tray on the major surface that receives and retains an insert dock 202 and a sensing module 200 during a measurement process. It should be noted that sensing insert device 100 is coupled to and provides measurement data in conjunction with other implanted prosthetic components. In other words, the prosthetic components are the permanent installed components of the patient.

Insert dock 202 is provided in different sizes and shapes. Insert dock 202 can comprise many different sizes and shapes to interface appropriately with different manufacturer prosthetic components. Prosthetic components are made in different sizes to accommodate anatomical differences over a wide population range. Insert dock 202 is designed for different prosthetic sizes within the same manufacturer. In at least one embodiment, multiple docks of different dimensions are provided for a surgery. For example, the thickness of the final insert is determined by the surgical cuts to the muscular-skeletal system and measurements provided by sensing module 200. The surgeon may try two insert docks 202 of different thicknesses before making a final decision. In one embodiment, sensing insert device 100 selected by the surgeon has substantially equal dimensions to the final insert used. In general, insert dock 202 allows standardization on a single sensing module 200 for different prosthetic platforms. Thus, the sensing module 200 is common to the different insert docks 202 allowing improved quality, reliability, and performance.

In one embodiment, one or more insert docks 202 are used to determine an appropriate thickness that yields an optimal loading. In general, the absolute loading over the range of motion is kept within a predetermined range. Soft tissue tensioning can be used to adjust the absolute loading. The knee balance can also be adjusted within a predetermined range if a total knee reconstruction is being performed and a sensing module 202 is used in each compartment. Tibial prosthetic component 106 and device 100 have a combined thickness that represents a combined thickness of tibial prosthetic component 106 and a final (or chronic) insert of the knee joint. Thus, the final insert thickness or depth is chosen based on the trial performed using device 100. Typically, the final insert thickness is identical to the device 100 to maintain the measured loading and balance. In one embodiment, sensing module 200 and insert docks 202 are disposed of after surgery. Alternatively, the sensing module 200 and insert docks 202 can be cleaned, sterilized, and packaged for reuse.

The prosthesis incorporating device 100 emulates the function of a natural knee joint. Device 100 can measure loads or other parameters at various points throughout the range of motion. Data from device 100 is transmitted to a receiving station 110 via wired or wireless communications. In a first embodiment, device 100 is a disposable system. Device 100 can be disposed of after using the sensing insert device 100 to optimally fit the joint implant. Device 100 is a low cost disposable system that reduces capital costs, operating costs, facilitates rapid adoption of quantitative measurement, and initiates evidentiary based orthopedic medicine. In a second embodiment, a methodology can be put in place to clean and sterilize device 100 for reuse. In a third embodiment, device 100 can be incorporated in a tool instead of being a component of the replacement joint. The tool can be disposable or be cleaned and sterilized for reuse. In a fourth embodiment, device 100 can be a permanent component of the replacement joint. Device 100 can be used to provide both short term and long term post-operative data on the implanted joint. In a fifth embodiment, device 100 can be coupled to the muscular-skeletal system. In all of the embodiments, receiving station 110 can include data processing, storage, or display, or combination thereof and provide real time graphical representation of the level and distribution of the load. Receiving station 110 can record and provide accounting information of device 100 to an appropriate authority.

The sensing insert device 100, in one embodiment, comprises a load sensing platform 121, an accelerometer 122, and sensing assemblies 123. This permits the sensing device 100 to assess a total load on the prosthetic components when it is being moved. The system accounts for forces due to gravity and motion. In one embodiment, load sensing platform 121 includes two or more load bearing surfaces, at least one energy transducer, at least one compressible energy propagating structure, and at least one member for elastic support. The accelerometer 122 can measure acceleration. Acceleration can occur when the sensing device 100 is moved or put in motion. Accelerometer 122 can sense orientation, vibration, and impact. In another embodiment, the femoral component 104 can similarly include an accelerometer 135, which by way of a communication interface to the sensing insert device 100, can provide reference position and acceleration data to determine an exact angular relationship between the femur and tibia. The sensing assemblies 123 can reveal changes in length or compression of the energy propagating structure or structures by way of the energy transducer or transducers. Together the load sensing platform 121, accelerometer 122 (and in certain cases accelerometer 135), and sensing assemblies 123 measure force or pressure external to the load sensing platform 121 or displacement produced by contact with the prosthetic components.

In at least one exemplary embodiment, an energy pulse is directed within one or more waveguides in device 100 by way of pulse mode operations and pulse shaping. The waveguide is a conduit that directs the energy pulse in a predetermined direction. The energy pulse is typically confined within the waveguide. In one embodiment, the waveguide comprises a polymer material. For example, urethane or polyethylene are polymers suitable for forming a waveguide. The polymer waveguide can be compressed and has little or no hysteresis in the system. Alternatively, the energy pulse can be directed through the muscular-skeletal system. In one embodiment, the energy pulse is directed through bone of the muscular-skeletal system to measure bone density. A transit time of an energy pulse is related to the material properties of a medium through which it traverses. This relationship is used to generate accurate measurements of parameters such as distance, weight, strain, pressure, wear, vibration, viscosity, and density to name but a few.

Incorporating data from the accelerometer 122 with data from the other sensing components 121 and 123 assures accurate measurement of the applied load, force, pressure, or displacement by enabling computation of adjustments to offset this external motion. This capability can be required in situations wherein the body, instrument, appliance, vehicle, equipment, or other physical system, is itself operating or moving during sensing of load, pressure, or displacement. This capability can also be required in situations wherein the body, instrument, appliance, vehicle, equipment, or other physical system, is causing the portion of the body, instrument, appliance, vehicle, equipment, or other physical system being measured to be in motion during sensing of load, pressure, or displacement.

The accelerometer 122 can operate singly, as an integrated unit with the load sensing platform 121, and/or as an integrated unit with the sensing assemblies 123. Integrating one or more accelerometers 122 within the sensing assemblages 123 to determine position, attitude, movement, or acceleration of sensing assemblages 123 enables augmentation of presentation of data to accurately identify, but not limited to, orientation or spatial distribution of load, force, pressure, displacement, density, or viscosity, or localized temperature by controlling the load and position sensing assemblages to measure the parameter or parameters of interest relative to specific orientation, alignment, direction, or position as well as movement, rotation, or acceleration along any axis or combination of axes. Measurement of the parameter or parameters of interest may also be made relative to the earth's surface and thus enable computation and presentation of spatial distributions of the measured parameter or parameters relative to this frame of reference.

In one embodiment, the accelerometer 122 includes direct current (DC) sensitivity to measure static gravitational pull with load and position sensing assemblages to enable capture of, but not limited to, distributions of load, force, pressure, displacement, movement, rotation, or acceleration by controlling the sensing assemblages to measure the parameter or parameters of interest relative to orientations with respect to the earths surface or center and thus enable computation and presentation of spatial distributions of the measured parameter or parameters relative to this frame of reference.

Embodiments of device 100 are broadly directed to measurement of physical parameters, and more particularly, to evaluating changes in the transit time of a pulsed energy wave propagating through a medium. In-situ measurements during orthopedic joint implant surgery would be of substantial benefit to verify an implant is in balance and under appropriate loading or tension. In one embodiment, the instrument is similar to and operates familiarly with other instruments currently used by surgeons. This will increase acceptance and reduce the adoption cycle for a new technology. The measurements will allow the surgeon to ensure that the implanted components are installed within predetermined ranges that maximize the working life of the joint prosthesis and reduce costly revisions. Providing quantitative measurement and assessment of the procedure using real-time data will produce results that are more consistent. A further issue is that there is little or no implant data generated from the implant surgery, post-operatively, and long term. Device 100 can provide implant status data to the orthopedic manufacturers and surgeons. Moreover, data generated by direct measurement of the implanted joint itself would greatly improve the knowledge of implanted joint operation and joint wear thereby leading to improved design and materials.

As mentioned previously, device 100 can be used for other joint surgeries; it is not limited to knee replacement implant or implants. Moreover, device 100 is not limited to trial measurements. Device 100 can be incorporated into the final joint system to provide data post-operatively to determine if the implanted joint is functioning correctly. Early determination of a problem using device 100 can reduce catastrophic failure of the joint by bringing awareness to a problem that the patient cannot detect. The problem can often be rectified with a minimal invasive procedure at lower cost and stress to the patient. Similarly, longer term monitoring of the joint can determine wear or misalignment that if detected early can be adjusted for optimal life or replacement of a wear surface with minimal surgery thereby extending the life of the implant. In general, device 100 can be shaped such that it can be placed or engaged or affixed to or within load bearing surfaces used in many orthopedic applications (or used in any orthopedic application) related to the musculoskeletal system, joints, and tools associated therewith. Device 100 can provide information on a combination of one or more performance parameters of interest such as wear, stress, kinematics, kinetics, fixation strength, ligament balance, anatomical fit and balance.

Figure 3:
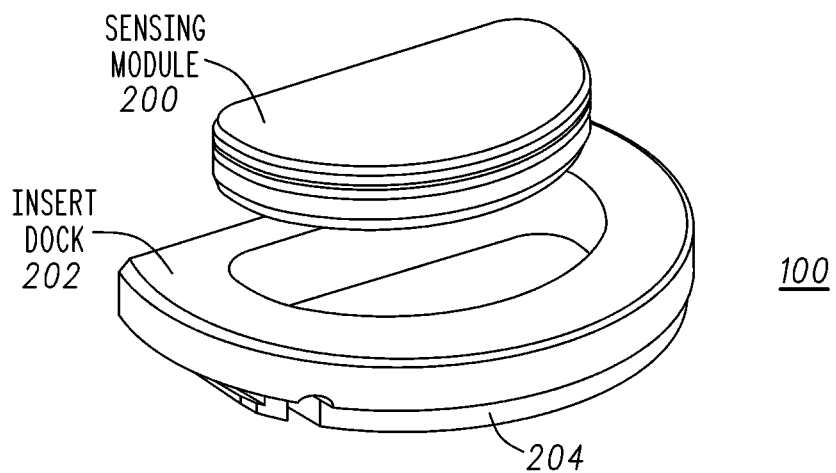
FIG. 3 is a perspective view of a medical sensing platform comprising an encapsulating enclosure in accordance with one embodiment.

FIG. 3 is a perspective view of a medical sensing platform comprising an encapsulating enclosure in accordance with one embodiment. In general, parameters of the muscular-skeletal system can be measured with a sensing module 200 that in one embodiment is an integral part of a complete sensing insert device 100. The sensing module 200 is a self-contained sensor within an encapsulating enclosure that integrates sensing assemblages, an electronic assemblage that couples to the sensing assemblages, a power source, signal processing, and wireless communication. All components required for the measurement are contained in the sensing module 200. The sensing module 200 has at least one contacting surface for coupling to the muscular-skeletal system. A parameter of the muscular-skeletal system is applied to the contact surfaces to be measured by the one or more sensing assemblages therein. As will be disclosed in further detail herein, the sensing module 200 is part of a system that allows intra-operative and post-operative sensing of a joint of the muscular-skeletal system. More specifically, sensing module 200 is placed within a temporary or permanent prosthetic component that has a similar form factor as the passive prosthetic component currently being used. This has a benefit of rapid adoption because the sensing platform is inserted identically to the commonly used passive component but can provide much needed quantitative measurements with little or no procedural changes.

As shown, the sensing insert device 100 comprises an insert dock 202 and the sensing module 200. Sensing insert device 100 is a non-permanent or temporary measurement device that is used intra-operatively to provide quantitative data related to the installation of prosthetic components such as in joint replacement surgery. The combination of the insert dock 202 and sensing module 202 has a form factor substantially equal to a final insert device. The final insert device can be a passive component or sensored incorporating sensing module 200. The substantially equal form factor of sensing insert device 100 results in no extraneous structures in the surgical field that can interfere with the procedure. For example, a final insert device is designed to mimic the function of the natural component it is replacing. The final insert device allows natural movement of the muscular-skeletal system and does not interfere with ligaments, tendons, tissue, muscles, and other components of the muscular-skeletal system. Similarly, sensing insert device 100 allows exposure of the surgical field around the joint by having the similar form factor as the final insert thereby allowing the surgeon to make adjustments during the installation in a natural setting with quantitative measurements to support the modifications.

In one embodiment, insert dock 202 is an adaptor. Insert dock 202 is made in different sizes. In general, prosthetic components are manufactured in different sizes to accommodate variation in the muscular-skeletal system from person to person. In the example, the size of insert dock 202 is chosen to mate with the selected prosthetic implant components. In particular, a feature 204 aligns with and retains insert dock 202 in a fixed position to a prosthetic or natural component of the muscular-skeletal system. The insert dock 202 is a passive component having an opening for receiving sensing module 200. The opening is positioned to place the contacting surfaces in a proper orientation to measure the parameter when used in conjunction with other prosthetic components. The insert dock 202 as an adaptor can be manufactured at low cost. Moreover, insert dock 202 can be formed for adapting to different prosthetic manufacturers thereby increasing system flexibility. This allows a standard sensing module 200 to be provided but customized for appropriate size and dimensions through dock 202 for the specific application and manufacturer component.

The one or more sensing assemblages within sensing module 200 couple to the contacting surfaces of sensing module 200 for receiving the applied parameter of the muscular-skeletal system. In one embodiment, a sensing assemblage comprises one or more energy transducers coupled to an elastic structure. The elastic structure allows the propagation of energy waves. The forms of energy propagated through the elastic energy propagating structures may include, but is not limited to, sound, ultrasound, or electromagnetic radiation including radio frequency, infrared, or light. A change in the parameter applied to the contacting surfaces results in a change a dimension of the elastic structure. The dimension of the elastic structure can be measured precisely using continuous wave, pulsed, or pulsed echo measurement. The dimension and material properties of the elastic structure have a known relationship to the parameter being measured. Thus, the dimension is precisely measured and converted to the parameter. Other factors such as movement or acceleration can be taken into account in the calculation. As an example, a force, pressure, or load applied to the one or more contacting surfaces of sensing module 200 is used to illustrate a parameter measurement hereinbelow. It should be noted that this is for illustration purposes and that the sensing module 200 can be used to measure other parameters.

As will be shown ahead, the encapsulating enclosure can serve in a first embodiment as a trial implant for orthopedic surgical procedures, namely, for determining load forces on prosthetic components and the musculoskeletal system. In a second embodiment, the encapsulating enclosure can be placed within a permanent prosthetic component for long term monitoring. The encapsulating enclosure supports and protects internal mechanical and electronic components from external physical, mechanical, chemical, and electrical, and electromagnetic intrusion that might compromise sensing or communication operations of the module or device. The integration of the internal components is designed to minimize adverse physical, mechanical, electrical, and ultrasonic interactions that might compromise sensing or communication operations of the module or device.

Figure 4:
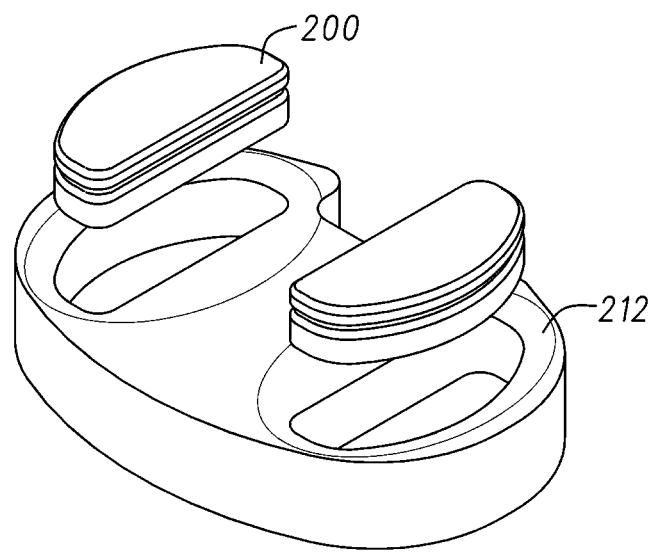
FIG. 4 is a perspective view of a medical sensing device suitable for use as a bi-compartmental implant and comprising an encapsulating enclosure in accordance with one embodiment.

FIG. 4 is a perspective view of a medical sensing device suitable for use as a bi-compartmental implant and comprising an encapsulating enclosure in accordance with one embodiment. As shown, the sensing insert device 100 comprises two sensing modules 200. Each sensing module 200 is a self-contained encapsulated enclosure that can make individual or coordinated parameter measurements. For example, the sensing insert device 100 can be used to assess load forces on a bi-compartmental knee joint implant. In particular, both sensing modules 200 can individually, or in combination, report applied loading forces. Bi-compartmental sensing provides the benefit of providing quantitative measurement to balance each compartment in relation to one another.

Similar to that described above, insert dock 202 is an adaptor having two openings instead of one. Insert dock 202 can be made in different sizes to accommodated different sized prosthetic components and different manufacturers. The insert dock 202 with two openings is a passive component for receiving two separate sensing modules 200. The opening is positioned to place the contacting surfaces in a proper orientation to measure the parameter when used in conjunction with other prosthetic components. In general, encapsulated enclosures can be positioned on or within, or engaged with, or attached or affixed to or within, a wide range of physical systems including, but not limited to instruments, appliances, vehicles, equipments, or other physical systems as well as animal and human bodies, for sensing and communicating the parameter or parameters of interest in real time. Similar to that described above, insert dock 202 as an adaptor can be manufactured at low cost providing design flexibility and allowing rapid adoption of quantitative measurement.

Figure 5:
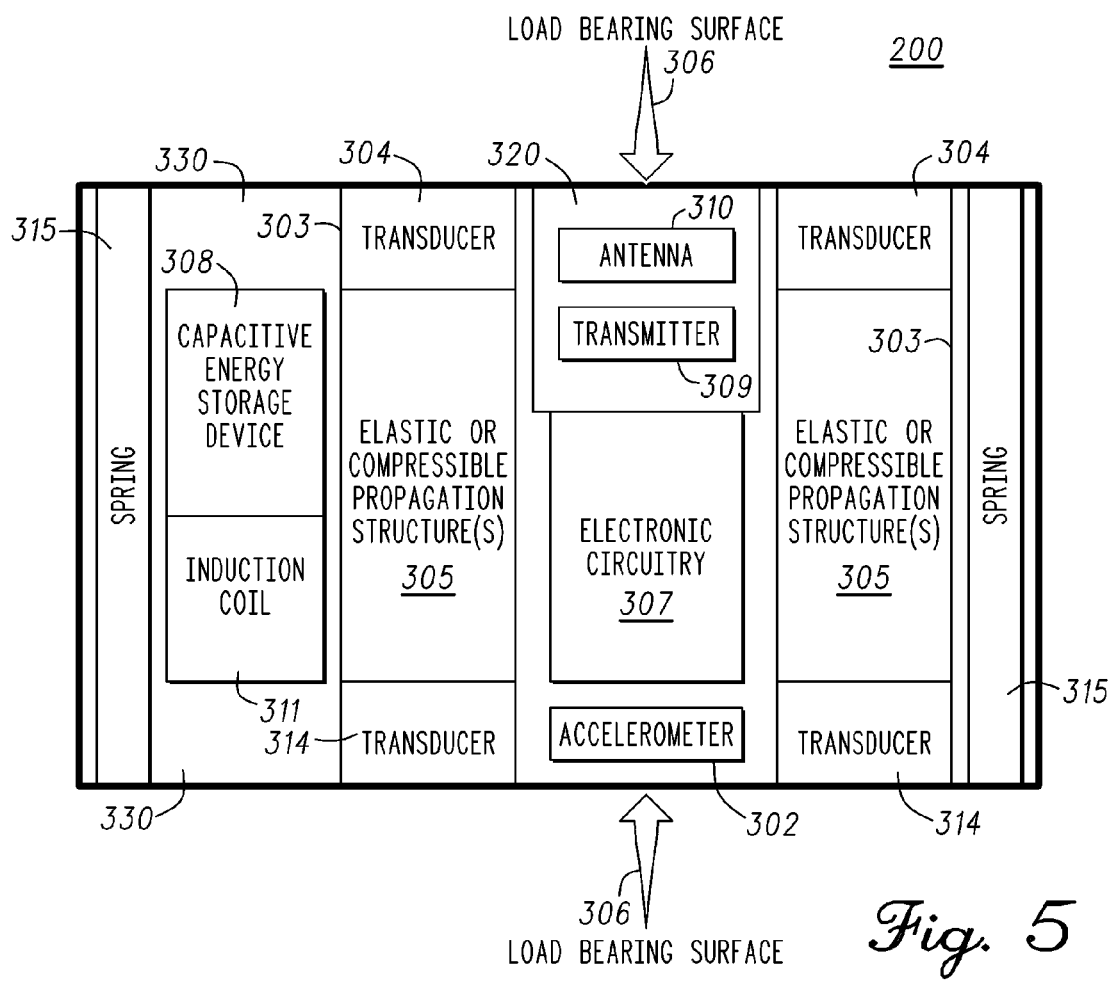
FIG. 5 is an exemplary block diagram of the components of the sensing module in accordance with an exemplary embodiment.

FIG. 5 is an exemplary block diagram of the components of the sensing module 200 in accordance with an exemplary embodiment. It should be noted that the sensing module could comprise more or less than the number of components shown. As illustrated, the sensing module includes one or more sensing assemblages 303, a transceiver 320, an energy storage 330, electronic circuitry 307, one or more mechanical supports 315 (e.g., springs), and an accelerometer 302. In the non-limiting example, an applied compressive force can be measured by the sensing module.

The sensing assemblage 303 can be positioned, engaged, attached, or affixed to the contact surfaces 306. Mechanical supports 315 serve to provide proper balancing of contact surfaces 306. In at least one exemplary embodiment, contact surfaces 306 are load-bearing surfaces. In general, the propagation structure 305 is subject to the parameter being measured. Surfaces 306 can move and tilt with changes in applied load; actions which can be transferred to the sensing assemblages 303 and measured by the electronic circuitry 307. The electronic circuitry 307 measures physical changes in the sensing assemblage 303 to determine parameters of interest, for example a level, distribution and direction of forces acting on the contact surfaces 306. In general, the sensing module is powered by the energy storage 330.

As one example, the sensing assemblage 303 can comprise an elastic or compressible propagation structure 305 between a transducer 304 and a transducer 314. In the current example, transducer 304 can be an ultrasound (or ultrasonic) resonator, and the elastic or compressible propagation structure 305 can be an ultrasound (or ultrasonic) waveguide (or waveguides). The electronic circuitry 307 is electrically coupled to the sensing assemblages 303 and translates changes in the length (or compression or extension) of the sensing assemblages 303 to parameters of interest, such as force. It measures a change in the length of the propagation structure 305 (e.g., waveguide) responsive to an applied force and converts this change into electrical signals which can be transmitted via the transceiver 320 to convey a level and a direction of the applied force. In other arrangements herein contemplated, the sensing assemblage 303 may require only a single transducer. In yet other arrangements, the sensing assemblage 303 can include piezoelectric, capacitive, optical or temperature sensors or transducers to measure the compression or displacement. It is not limited to ultrasonic transducers and waveguides.

The accelerometer 302 can measure acceleration and static gravitational pull. Accelerometer 302 can be single-axis and multi-axis accelerometer structures that detect magnitude and direction of the acceleration as a vector quantity. Accelerometer 302 can also be used to sense orientation, vibration, impact and shock. The electronic circuitry 307 in conjunction with the accelerometer 302 and sensing assemblies 303 can measure parameters of interest (e.g., distributions of load, force, pressure, displacement, movement, rotation, torque and acceleration) relative to orientations of the sensing module with respect to a reference point. In such an arrangement, spatial distributions of the measured parameters relative to a chosen frame of reference can be computed and presented for real-time display.

The transceiver 320 comprises a transmitter 309 and an antenna 310 to permit wireless operation and telemetry functions. In various embodiments, the antenna 310 can be configured by design as an integrated loop antenna. As will be explained ahead, the integrated loop antenna is configured at various layers and locations on the electronic substrate with electrical components and by way of electronic control circuitry to conduct efficiently at low power levels. Once initiated the transceiver 320 can broadcast the parameters of interest in real-time. The telemetry data can be received and decoded with various receivers, or with a custom receiver. The wireless operation can eliminate distortion of, or limitations on, measurements caused by the potential for physical interference by, or limitations imposed by, wiring and cables connecting the sensing module with a power source or with associated data collection, storage, display equipment, and data processing equipment.

The transceiver 320 receives power from the energy storage 330 and can operate at low power over various radio frequencies by way of efficient power management schemes, for example, incorporated within the electronic circuitry 307. As one example, the transceiver 320 can transmit data at selected frequencies in a chosen mode of emission by way of the antenna 310. The selected frequencies can include, but are not limited to, ISM bands recognized in International Telecommunication Union regions 1, 2 and 3. A chosen mode of emission can be, but is not limited to, Gaussian Frequency Shift Keying, (GFSK), Amplitude Shift Keying (ASK), Phase Shift Keying (PSK), Minimum Shift Keying (MSK), Frequency Modulation (FM), Amplitude Modulation (AM), or other versions of frequency or amplitude modulation (e.g., binary, coherent, quadrature, etc.).

The antenna 310 can be integrated with components of the sensing module to provide the radio frequency transmission. The substrate for the antenna 310 and electrical connections with the electronic circuitry 307 can further include a matching network. This level of integration of the antenna and electronics enables reductions in the size and cost of wireless equipment. Potential applications may include, but are not limited to any type of short-range handheld, wearable, or other portable communication equipment where compact antennas are commonly used. This includes disposable modules or devices as well as reusable modules or devices and modules or devices for long-term use.

The energy storage 330 provides power to electronic components of the sensing module. It can be charged by wired energy transfer, short-distance wireless energy transfer or a combination thereof. External power sources can include, but are not limited to, a battery or batteries, an alternating current power supply, a radio frequency receiver, an electromagnetic induction coil, a photoelectric cell or cells, a thermocouple or thermocouples, or an ultrasound transducer or transducers. By way of the energy storage 330, the sensing module can be operated with a single charge until the internal energy is drained. It can be recharged periodically to enable continuous operation. The energy storage 330 can utilize power management technologies such as replaceable batteries, supply regulation technologies, and charging system technologies for supplying energy to the components of the sensing module to facilitate wireless applications.

The energy storage 330 minimizes additional sources of energy radiation required to power the sensing module during measurement operations. In one embodiment, as illustrated, the energy storage 330 can include a capacitive energy storage device 308 and an induction coil 311. External source of charging power can be coupled wirelessly to the capacitive energy storage device 308 through the electromagnetic induction coil or coils 311 by way of inductive charging. The charging operation can be controlled by power management systems designed into, or with, the electronic circuitry 307. As one example, during operation of electronic circuitry 307, power can be transferred from capacitive energy storage device 308 by way of efficient step-up and step-down voltage conversion circuitry. This conserves operating power of circuit blocks at a minimum voltage level to support the required level of performance.

In one configuration, the energy storage 330 can further serve to communicate downlink data to the transceiver 320 during a recharging operation. For instance, downlink control data can be modulated onto the energy source signal and thereafter demodulated from the induction coil 311 by way of electronic control circuitry 307. This can serve as a more efficient way for receiving downlink data instead of configuring the transceiver 320 for both uplink and downlink operation. As one example, downlink data can include updated control parameters that the sensing module uses when making a measurement, such as external positional information, or for recalibration purposes, such as spring biasing. It can also be used to download a serial number or other identification data.

The electronic circuitry 307 manages and controls various operations of the components of the sensing module, such as sensing, power management, telemetry, and acceleration sensing. It can include analog circuits, digital circuits, integrated circuits, discrete components, or any combination thereof. In one arrangement, it can be partitioned among integrated circuits and discrete components to minimize power consumption without compromising performance. Partitioning functions between digital and analog circuit enhances design flexibility and facilitates minimizing power consumption without sacrificing functionality or performance. Accordingly, the electronic circuitry 307 can comprise one or more Application Specific Integrated Circuit (ASIC) chips, for example, specific to a core signal processing algorithm.

In another arrangement, the electronic circuitry can comprise a controller such as a programmable processor, a Digital Signal Processor (DSP), a microcontroller, or a microprocessor, with associated storage memory and logic. The controller can utilize computing technologies with associated storage memory such a Flash, ROM, RAM, SRAM, DRAM or other like technologies for controlling operations of the aforementioned components of the sensing module. In one arrangement, the storage memory may store one or more sets of instructions (e.g., software) embodying any one or more of the methodologies or functions described herein. The instructions may also reside, completely or at least partially, within other memory, and/or a processor during execution thereof by another processor or computer system.

The electronics assemblage also supports testability and calibration features that assure the quality, accuracy, and reliability of the completed wireless sensing module or device. A temporary bi-directional interconnect assures a high level of electrical observability and controllability of the electronics. The test interconnect also provides a high level of electrical observability of the sensing subsystem, including the transducers, waveguides, and mechanical spring or elastic assembly. Carriers or fixtures emulate the final enclosure of the completed wireless sensing module or device during manufacturing processing, thus enabling capture of accurate calibration data for the calibrated parameters of the finished wireless sensing module or device. These calibration parameters are stored within the on-board memory integrated into the electronics assemblage.

Applications for sensing module 200 may include, but are not limited to, disposable modules or devices as well as reusable modules or devices and modules or devices for long-term use. In addition to non-medical applications, examples of a wide range of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

Figure 6:
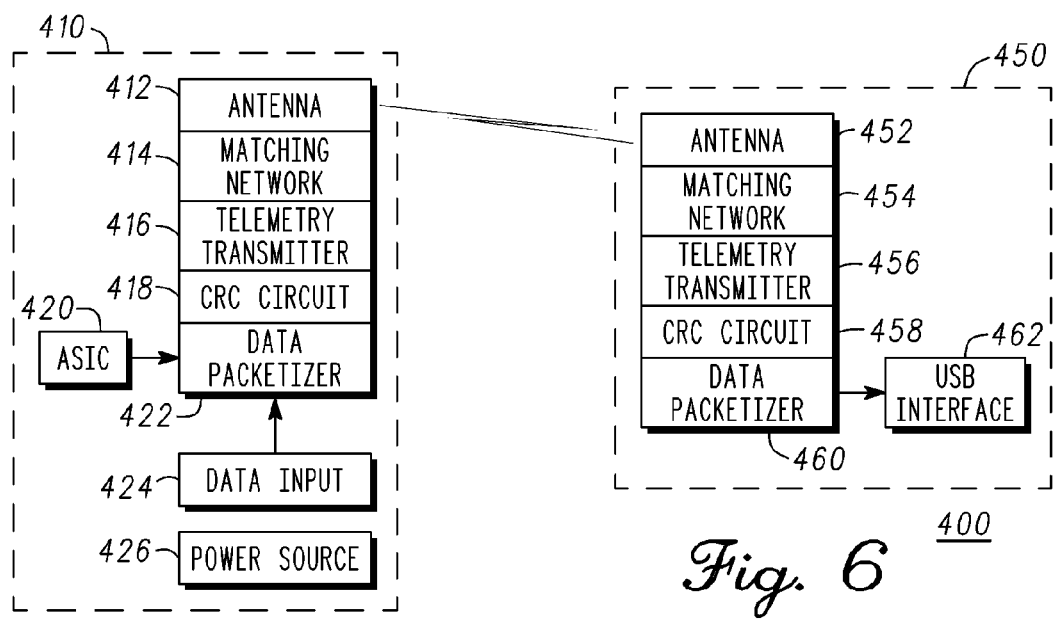
FIG. 6 is a diagram of an exemplary communications system for short-range telemetry according to one embodiment.

FIG. 6 is a diagram of an exemplary communications system 400 for short-range telemetry according to one embodiment. As illustrated, the exemplary communications system 400 comprises medical device communications components 410 of the sensing insert device 100 (see FIG. 1) and receiving system communications components 450 of the receiving system 110 (see FIG. 1). The medical device communications components 410 are inter-operatively coupled to include, but not limited to, the antenna 412, a matching network 414, the telemetry transceiver 416, a CRC circuit 418, a data packetizer 422, a data input 424, a power source 426, and an application specific integrated circuit (ASIC) 420. The medical device communications components 410 may include more or less than the number of components shown and are not limited to those shown or the order of the components.

The receiving station communications components 450 comprise an antenna 452, the matching network 454, the telemetry receiver 456, the CRC circuit 458, the data packetizer 460, and optionally a USB interface 462. Notably, other interface systems can be directly coupled to the data packetizer 460 for processing and rendering sensor data.

With respect to FIG. 1, in view of the communication components of FIG. 6, the sensing insert device 100 acquires sensor data by way of the data input to the ASIC 420. Referring briefly to FIG. 5, the ASIC 420 is operatively coupled to sensing assemblies 303. In one embodiment, a change in the parameter being measured by device 100 produces a change in a length of a compressible propagation structure 305. ASIC 420 controls the emission of energy waves into propagation structure 305 and the detection of propagated energy waves. ASIC 420 generates data related to transit time, frequency, or phase of propagated energy waves. The data corresponds to the length of propagation structure 305, which can be translated to the parameter of interest by way of a known function or relationship. Similarly, the data can comprise voltage or current measurements from a MEMS structure, piezo-resistive sensor, strain gauge, or other sensor type that is used to measure the parameter. The data packetizer 422 assembles the sensor data into packets; this includes sensor information received or processed by ASIC 420. The ASIC 420 can comprise specific modules for efficiently performing core signal processing functions of the medical device communications components 410. The ASIC 420 provides the further benefit of reducing the form factor of sensing insert device 100 to meet dimensional requirements for integration into temporary or permanent prosthetic components.

The CRC circuit 418 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The telemetry transmitter 416 then transmits the CRC encoded data packet through the matching network 414 by way of the antenna 412. The matching networks 414 and 454 provide an impedance match for achieving optimal communication power efficiency.

The receiving system communications components 450 receive transmission sent by medical device communications components 410. In one embodiment, telemetry transmitter 416 is operated in conjunction with a dedicated telemetry receiver 456 that is constrained to receive a data stream broadcast on the specified frequencies in the specified mode of emission. The telemetry receiver 456 by way of the receiving station antenna 452 detects incoming transmissions at the specified frequencies. The antenna 452 can be a directional antenna that is directed to a directional antenna of components 410. Using at least one directional antenna can reduce data corruption while increasing data security by further limiting where the data is radiated. A matching network 454 couples to antenna 452 to provide an impedance match that efficiently transfers the signal from antenna 452 to telemetry receiver 456. Telemetry receiver 456 can reduce a carrier frequency in one or more steps and strip off the information or data sent by components 410. Telemetry receiver 456 couples to CRC circuit 458. CRC circuit 458 verifies the cyclic redundancy checksum for individual packets of data. CRC circuit 458 is coupled to data packetizer 460. Data packetizer 460 processes the individual packets of data. In general, the data that is verified by the CRC circuit 458 is decoded (e.g., unpacked) and forwarded to an external data processing device, such as an external computer, for subsequent processing, display, or storage or some combination of these.

The telemetry receiver 456 is designed and constructed to operate on very low power such as, but not limited to, the power available from the powered USB port 462, or a battery. In another embodiment, the telemetry receiver 456 is designed for use with a minimum of controllable functions to limit opportunities for inadvertent corruption or malicious tampering with received data. The telemetry receiver 456 can be designed and constructed to be compact, inexpensive, and easily manufactured with standard manufacturing processes while assuring consistently high levels of quality and reliability.

In one configuration, the communication system 400 operates in a transmit-only operation with a broadcasting range on the order of a few meters to provide high security and protection against any form of unauthorized or accidental query. The transmission range can be controlled by the transmitted signal strength, antenna selection, or a combination of both. A high repetition rate of transmission can be used in conjunction with the Cyclic Redundancy Check (CRC) bits embedded in the transmitted packets of data during data capture operations thereby enabling the receiving system 110 to discard corrupted data without materially affecting display of data or integrity of visual representation of data, including but not limited to measurements of load, force, pressure, displacement, flexion, attitude, and position within operating or static physical systems.

By limiting the operating range to distances on the order of a few meters the telemetry transmitter 416 can be operated at very low power in the appropriate emission mode or modes for the chosen operating frequencies without compromising the repetition rate of the transmission of data. This mode of operation also supports operation with compact antennas, such as an integrated loop antenna. The combination of low power and compact antennas enables the construction of, but is not limited to, highly compact telemetry transmitters that can be used for a wide range of non-medical and medical applications. Examples of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

The transmitter security as well as integrity of the transmitted data is assured by operating the telemetry system within predetermined conditions. The security of the transmitter cannot be compromised because it is operated in a transmit-only mode and there is no pathway to hack into medical device communications components 410. The integrity of the data is assured with the use of the CRC algorithm and the repetition rate of the measurements. The risk of unauthorized reception of the data is minimized by the limited broadcast range of the device. Even if unauthorized reception of the data packets should occur there are counter measures in place that further mitigate data access. A first measure is that the transmitted data packets contain only binary bits from a counter along with the CRC bits. A second measure is that no data is available or required to interpret the significance of the binary value broadcast at any time. A third measure that can be implemented is that no patient or device identification data is broadcast at any time.

The telemetry transmitter 416 can also operate in accordance with some FCC regulations. According to section 18.301 of the FCC regulations the ISM bands within the USA include 6.78, 13.56, 27.12, 30.68, 915, 2450, and 5800 MHz as well as 24.125, 61.25, 122.50, and 245 GHz. Globally other ISM bands, including 433 MHz, are defined by the International Telecommunications Union in some geographic locations. The list of prohibited frequency bands defined in 18.303 are "the following safety, search and rescue frequency bands is prohibited: 490-510 kHz, 2170-2194 kHz, 8354-8374 kHz, 121.4-121.6 MHz, 156.7-156.9 MHz, and 242.8-243.2 MHz." Section 18.305 stipulates the field strength and emission levels ISM equipment must not exceed when operated outside defined ISM bands. In summary, it may be concluded that ISM equipment may be operated worldwide within ISM bands as well as within most other frequency bands above 9 KHz given that the limits on field strengths and emission levels specified in section 18.305 are maintained by design or by active control. As an alternative, commercially available ISM transceivers, including commercially available integrated circuit ISM transceivers, may be designed to fulfill these field strengths and emission level requirements when used properly.

In one configuration, the telemetry transmitter 416 can also operate in unlicensed ISM bands or in unlicensed operation of low power equipment, wherein the ISM equipment (e.g., telemetry transmitter 416) may be operated on ANY frequency above 9 kHz except as indicated in Section 18.303 of the FCC code.

Wireless operation eliminates distortion of, or limitations on, measurements caused by the potential for physical interference by, or limitations imposed by, wiring and cables connecting the wireless sensing module or device with a power source or with data collection, storage, or display equipment. Power for the sensing components and electronic circuits is maintained within the wireless sensing module or device on an internal energy storage device. This energy storage device is charged with external power sources including, but not limited to, a battery or batteries, super capacitors, capacitors, an alternating current power supply, a radio frequency receiver, an electromagnetic induction coil, a photoelectric cell or cells, a thermocouple or thermocouples, or an ultrasound transducer or transducers. The wireless sensing module may be operated with a single charge until the internal energy source is drained or the energy source may be recharged periodically to enable continuous operation. The embedded power supply minimizes additional sources of energy radiation required to power the wireless sensing module or device during measurement operations. Telemetry functions are also integrated within the wireless sensing module or device. Once initiated the telemetry transmitter continuously broadcasts measurement data in real time. Telemetry data may be received and decoded with commercial receivers or with a simple, low cost custom receiver.

A method can be practiced with more or less than the number of steps shown and is not limited to the order shown. To describe the method, reference will be made to the components of FIG. 5, although it is understood that the method can be implemented in any other manner using other suitable components. Generally, method is directed to non-secure applications for one-way transmission communications, for example, where an implanted medical device or sensor transmits data to a receiving station (e.g., 110 see FIG. 1) but does not receive confirmation from the receiving station, although in various embodiments, the implanted medical device includes an integrated receiver for receiving confirmation and acknowledgement communications.

The method can start in a state wherein the sensing insert device 100 has been inserted and powered on, for example, within a knee prosthesis implant. The medical device can be powered on via manual intervention, for example, by the surgeon or technician implanting the medical device during a surgical procedure, or the device can turn on automatically after a duration of time or at certain time intervals, for example, 1 hour after manual activation, or every 10 seconds after power up, depending on an operating mode.

In a first step, the medical device acquires sensor data such as load information (e.g., force, location, duration, etc.) from the sensing module 200. The electronic circuitry 307 generates the load data by way of the sensing assemblies 303, for instance, by converting changes in length of ultrasonic propagation structures (waveguides) to force data. In a second step, the sensing module 200 evaluates data bounds on the load data. In a third step, sensing module 200 assigns priorities based on the data bounds. Sensor data outside a predetermined range or above a predefined threshold can be flagged with a priority or discarded. For example, sensor data that falls outside a safe range or exceeds a safe level (e.g., applied force level, angle of flexion, excessive rotation) is prioritized accordingly.

In a fourth step, the sensing module 200 generates a packet of data including the sensor data, priority, and any corresponding information. In a fifth step, the sensing module 200 determines its communications mode based on operating mode and priority level. The operating mode indicates whether the sensing module 200 is operating in a power saving mode (e.g., standby) or other power management mode and takes into account information such as remaining battery life and drain. In a sixth step, a Cyclic Redundancy Check (CRC) can be appended to the data packed. In other embodiments, more sophisticated forward error correction schemes (e.g., block coding, convolutional coding) can be applied along with secure encryption or key-exchange cryptographic protocols.

The cyclic redundancy check (CRC) is a non-secure form of message digest designed to detect accidental changes to raw computer data. The CRC step comprises calculating a short, fixed-length sequence, known as the CRC code, for each block of data and sends or stores them both together. When a block is read or received the receiving station 110 (FIG. 1) repeats the calculation; if the new CRC does not match the one sent (or in some cases, cancel it out) then the block contains a data error and the receiving station 110 may take corrective action such as rereading or requesting the block be sent again. Briefly, FIG. 13, illustrates an exemplary data packet 1300 containing sensor data (e.g., Fx, duration, location), a priority level (e.g., 1 to 10), and a CRC.

In a seventh step, the transceiver 320 then transmits the data packet based on the priority level and operating mode. For instance, a low priority data packet can be appended with previous low-priority data packets and then transmitted over a single communication channel as a data stream, or at staggered time intervals to conserve power (e.g., scheduled to transmit every 10 seconds). The bundled packet data can then be decoded at the receiving station 110 and thereafter processed accordingly. Alternatively, a high priority packet can be transmitted immediately instead of a delayed time or the scheduled transmit intervals. Depending on the communication mode (e.g., priority level, operating mode), the transceiver may transmit the same high priority packet multiple times in a redundant manner to guarantee receipt. This ensures that the data is received and processed at the receiving station 110 in the event an immediate course of action or response is necessary, for example, to ensure the patient's safety or to report a warning.

The sensor data can be transmitted at the selected frequencies in the chosen mode of emission by way of the antenna 310. In certain configurations, the antenna 310 is an integrated loop antenna designed into a substrate of the sensing module 200 for maximizing power efficiency. As an example the chosen frequencies can include, but are not limited to, ISM bands recognized in International Telecommunication Union regions 1, 2, and 3 and the chosen mode of emission may be, but is not limited to, Gaussian Frequency Shift Keying, (GFSK) or others version of frequency or amplitude shift keying or modulation.

The receiving station 110 (see FIG. 1) 110 receives packets of data broadcast in the specified mode of emission on the specified frequencies and verifies the cyclic redundancy check checksum for individual packets of data or bundled packet data. Data that cannot be verified may be discarded. Data that are verified are forward to an external data processing device, such as an external computer, for subsequent processing, display, or storage or combination thereof.

Figure 7:
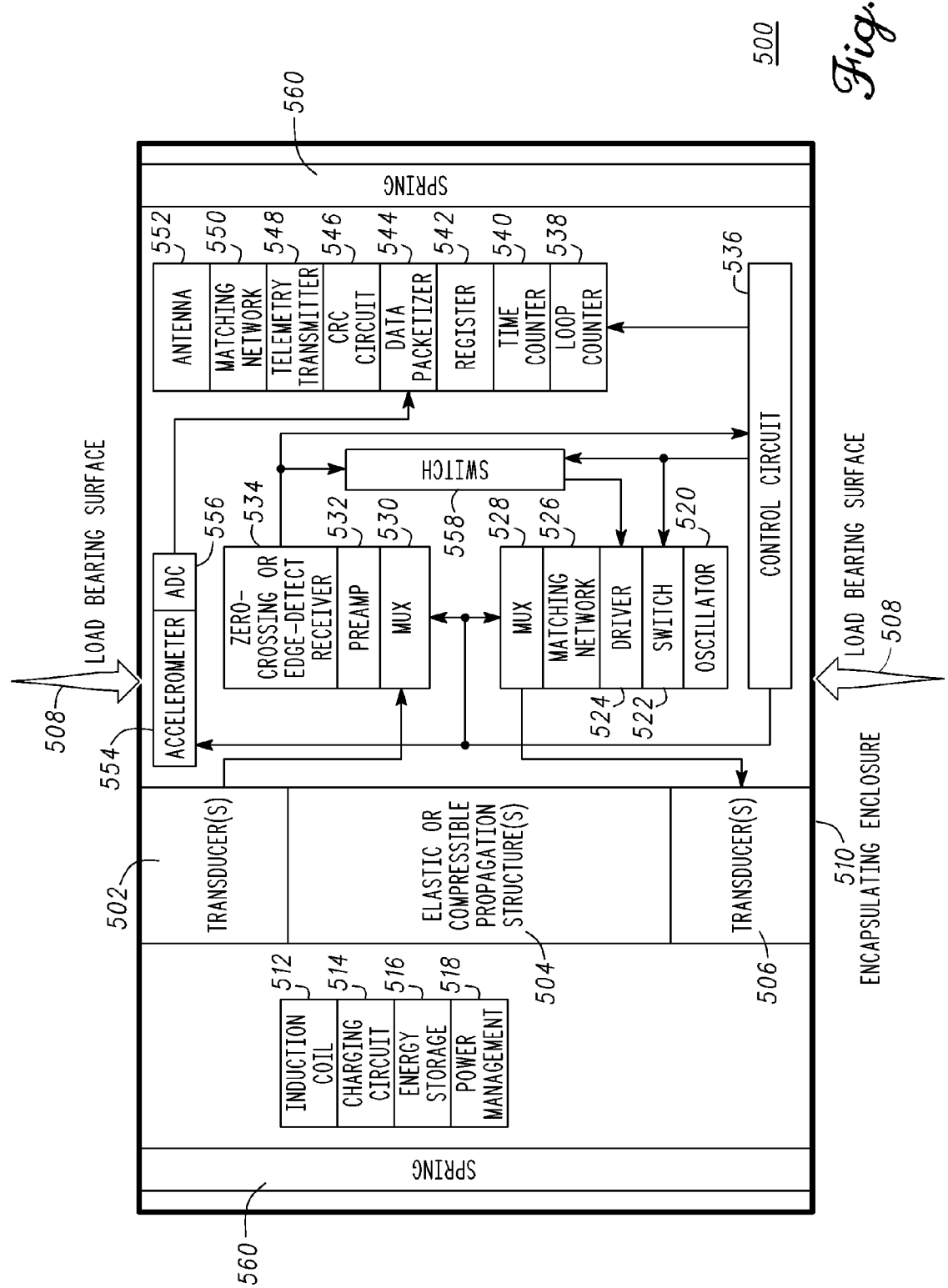
FIG. 7 is an illustration of a block model diagram of the sensing module in accordance with an exemplary embodiment.

FIG. 7 is an illustration of a block model diagram 500 of the sensing module 200 in accordance with an exemplary embodiment. In particular, the diagram 500 shows where certain components are replaced or supplemented with one or more Application Specific Integrated Circuits (ASICs). Referring briefly to FIG. 5, electronic circuitry 307 is coupled to the one or more sensing assemblages and includes circuitry that can control sensor operations. Electronic circuitry 307 includes multiple channels that can operate more than one device. Sensing module 200 is optimized to operate under severe power constraints. Electronic circuitry 307 includes power management circuitry that controls power up, power down, and minimizes power usage through the control of individual blocks. The architecture is designed to enable only blocks required for the current operation.

Referring back to FIG. 7, the ASIC provides significant benefit in reducing power requirements allowing the module 200 to be powered by a temporary power source such as a super capacitor or capacitor. The ASIC and super capacitor have a small form factor allowing module 200 to be integrated within a temporary or permanent prosthetic component. Module 200 incorporates one or more sensors comprising at least one transducer and a compressible media, the operation of which is disclosed in detail herein. As shown, a sensing assemblage comprises a transducer 502, compressible propagation structure 504, and a transducer 506. It should be noted that other sensors such as MEMS devices, strain gauges, and piezo-resistive sensors can be used with the ASIC. In particular, the ASIC incorporates A/D and D/A circuitry (not shown) to digitize current and voltage output from these types of sensing components. Transducers 502 and 506 operatively couple to compressible propagation structure 504. In a non-limiting example, transducer 506 to emits energy waves into compressible structure 504 while transducer 502 detects propagated energy waves. Compressible propagation structure 504 is coupled to a load bearing or contacting surface 508 and an encapsulating enclosure 510 of sensing module 200. A parameter to be measured is applied to either contacting surface 508, encapsulating enclosure 510, or both. In one embodiment, springs 560 couple to contacting surface 508 and encapsulating enclosure 510 to support compressible propagation structure 504. In particular, springs 560 prevent cantilevering of contacting surface 508, reduce hysteresis caused by material properties of compressible propagation structure 504, and improve sensor response time to changes in the applied parameter.

In one embodiment, a first ASIC includes a charging circuit 514 and power management circuitry 518. The power management circuitry 518 couples to the charging circuit, other blocks of the ASIC and external components/circuitry to minimize power consumption of the integrated circuit. The charging circuit 514 operatively couples to an induction coil 512 and energy storage 516. In a non-limiting example, induction coil 512 couples to an external coil that provides energy to charge energy storage 516. Induction coil 512 and the external coil are placed in proximity to each other thereby electro-magnetically coupling to one another. Induction coil 512 is coupled to energy storage 516. Charging circuit 514 controls the charging of energy storage 516. Charging circuit 514 can determine when charging is complete, monitor power available, and regulate a voltage provided to the operational circuitry. Charging circuit 514 can charge a battery in sensing module 200. Alternatively, a capacitor or super capacitor can be used to power the first ASIC for a time sufficient to acquire the desired measurements. A capacitor has the benefit of a long or indefinite shelf life and fast charge time. In either charging scenario, energy from the external coil is coupled to the induction coil 512. The energy from induction coil 512 is then stored in a medium such as a battery or capacitor.

Benefits of ultracapacitors, ultra capacitors, or super capacitors, or other form of capacitors as a power source instead or, or in conjunction with, other power sources or rechargeable technologies include, but are not limited to, enabling a high level of miniaturization as ultracapacitors, ultra capacitors, or super capacitors are smaller than smallest available battery for the same level of energy and power for many low power applications or applications that require power only intermittently or as a short-term backup for other power sources.

For applications that require power only intermittently, capacitors enable rapid recharge that is much faster than battery technologies and rechargeable chemistries regardless of their energy capacity. A charge time, from a completely uncharged state takes minutes because no chemical processes are involved in charging capacitors. This may be compared to charge times on the order of hours for many battery technologies that cannot be charged at a rate faster that one-half the energy storage capacity of the battery within one hour. In practice, many battery applications charge at a much slower rate. Many capacitors have the added benefit of almost indefinite lifetimes. There is no deterioration of a capacitor's storage capacity when uncharged, regardless of length of time at zero charge. Another benefit is that overcharging capacitors may pose less risk to electronics within an electronic module or device than overcharging batteries might pose. Furthermore, capacitors eliminate storage and disposal limitations of batteries with no risk of chemical leakage. In addition, capacitors can have a smaller form factor, are surface-mountable, and integrate well into the electronics assemblies and standard surface-mount electronic assembly processes.

Use capacitors to provide operating power for wireless devices, telemetry devices, or medical devices provides design, construction, and operating flexibility over a wide range of potential applications. Capacitors can be charged by connecting them to other power sources such as, but not limited to, a battery or batteries, an alternating current (AC) power supply, a radio frequency (RF) receiver, or an electromagnetic induction coil or coils, a photoelectric cell or cells, a thermocouple or thermocouples, capacitors, or an ultrasound transducer or transducers. For compact electronic modules or devices, ultracapacitors, super capacitors, or other form of capacitors provide many benefits over other rechargeable technologies.

The first ASIC further includes circuitry to operate and capture data from the sensing assemblages. A parameter to be measured is applied to compressible propagation structure 504. As an example of parameter measurement, a force, pressure, or load is applied across contacting surface 508 and encapsulating enclosure 510. The force, pressure, or load affects the length of the compressible propagation structure 504. The circuitry on the first ASIC forms a positive closed loop feedback circuit that maintains the emission, propagation, and detection of energy waves in the compressible propagation structure 504. The first ASIC operatively couples to transducers 502 and 506 to control the positive closed loop feedback circuit that is herein called a propagation tuned oscillator (PTO). The first ASIC measures a transit time, frequency, or phase of propagated energy waves. The measurement is used to determine the length of compressible propagation structure 504. The energy waves emitted into compressible propagation structure 504 can be continuous or pulsed. The energy waves can propagate by a direct path or be reflected.

The first ASIC comprises an oscillator 520, a switch 522, driver 524, matching network 526, MUX 528, and control circuit 536. The oscillator 520 is used as a reference clock for the ASIC and enables the PTO to begin emission of energy waves into the compressible propagation structure 504. Oscillator 520 in the first ASIC can be coupled to an external component such as a crystal oscillator to define and provide a stable frequency of operation. Switch 522 couples the oscillator 520 to MUX 528. Control circuit 536 operatively enables MUX 528 and switch 522 to couple oscillator 520 to driver 524 during a startup sequence. Driver 524 and matching network 526 couple to transducer 506. Driver 524 drives transducer 506 to emit an energy wave. Matching network 526 impedance matches driver 524 to the transducer 506 to reduce power consumption during energy wave emission.

In one embodiment, transducer 506 emits one or more energy waves into the compressible propagation structure 504 at a first location. Transducer 506 is located at a second location of compressible propagation structure 504. Transducer 506 detects propagated energy waves at the second location and generates a signal corresponding to the propagated energy waves. The first ASIC further comprises a MUX 530, pre-amplifier 532 (e.g. preamp 532) and a zero-crossing receiver or edge detect receiver. Zero-crossing receiver or edge-detect receiver comprise detect circuit 534. Control circuit 536 enables MUX 530 to couple transducer 502 to preamp 532. Preamp 532 amplifies a signal output by transducer 502 corresponding to a propagated energy wave. In a non-limiting example, the first ASIC comprises both a zero-crossing receiver and an edge detect receiver. More multiplexing circuitry in conjunction with control circuit 536 can be incorporated on the first ASIC to select between the circuits. Similarly, multiplexing circuitry can be used to couple and operate more than one sensor. The amplified signal from preamp 532 is coupled to detection circuit 534. Zero-crossing receiver is a detection circuit that identifies a propagated energy wave by sensing a transition of the signal. A requirement of detection can be that the signal has certain transition and magnitude characteristics. The edge-detect receiver detects a propagated energy wave by identifying a wave front of the propagated energy wave. The zero-crossing receiver or edge-detect receiver outputs a pulse in response to the detection of a propagated energy wave.

Positive closed loop feedback is applied upon detection of an energy wave after the startup sequence. Control circuit 536 decouples oscillator 520 from driver 524 through switch 522 and MUX 528. Control circuit 536 operatively enables switch 558 and MUX 528 to couple detection circuit 534 to driver 524. A pulse generated by detection circuit 534 initiates the emission of a new energy wave into compressible propagation structure 504. The pulse from detection circuit 534 is provided to driver 524. The positive closed loop feedback of the circuitry maintains the emission, propagation, and detection of energy waves in propagation structure 504.

The first ASIC further comprises a loop counter 538, time counter 540, register 542, and ADC 556. Loop counter 538, time counter 540, and register 542 are operatively coupled to control circuit 536 to generate a precise measurement of the transit time, frequency, or phase of propagated energy waves during a measurement sequence. In one embodiment, a measurement comprises a predetermined number of energy waves propagating through the compressible propagation structure 504. The predetermined number is set in the loop counter 538. The loop counter 538 is decremented by each pulse output by detection circuit 534 that corresponds to a detected propagated energy wave. The positive closed loop feedback is broken when counter 538 decrements to zero thereby stopping the measurement. Time counter 540 measures a total propagation time of the predetermined number of propagated energy waves set in loop counter 538. The measured total propagation time divided by the predetermined number of propagated energy waves is a measured transit time of an energy wave. The measured transit time can be precisely converted to a length of compressible propagation structure 504 under a stable condition of the applied parameter on the sensing assemblage. The applied parameter value can be calculated by known relationship between the length of compressible propagation structure 504 and the parameter. A result of the measurement is stored in register 542 when loop counter 538 decrements to zero. More than one measurement can be performed and stored. In one embodiment, the precision can be increased by raising the number of propagated energy waves being measured in loop counter 538.

In the example, energy waves are propagated from transducer 506 to transducer 5. Alternatively, control circuit 536 can direct the propagation of energy waves from transducer 502 to transducer 506 whereby transducer 502 emits energy waves and transducer 506 detects propagated energy waves. An analog to digital converter (ADC) 556 is shown coupled to an accelerometer 554. ADC 556 is a circuit on the first ASIC. It can be used to digitize an output from a circuit such as accelerometer 554. Accelerometer 554 can be used to detect and measure when sensing module 200 is in motion. Data from accelerometer 554 can be used to correct the measured result to account for module 200 acceleration. ADC 556 can also be used to provide measurement data from other sensor types by providing a digitized output corresponding to voltage or current magnitude.

A second ASIC can comprise CRC circuit 546, telemetry transmitter 548, and matching network 508. The CRC circuit 546 applies error code detection on the packet data such as data stored in register 542. The cyclic redundancy check computes a checksum for a data stream or packet of any length. The checksums are used to detect interference or accidental alteration of data during transmission. Transmitter 548 is coupled to CRC 546 and sends the data wirelessly. Matching network 550 couples telemetry transmitter 512 to antenna 552 to provide an impedance match to efficiently transfer the signal to the antenna 552. As disclosed above, the integration of the telemetry transmitter and sensor modules enables construction of a wide range of sizes of the sensing module 200. This facilitates capturing data, measuring parameters of interest and digitizing that data, and subsequently communicating that data to external equipment with minimal disturbance to the operation of the body, instrument, appliance, vehicle, equipment, or physical system for a wide range of applications. Moreover, the level of accuracy and resolution achieved by the total integration of communication components, transducers, waveguides, and oscillators to control the operating frequency of the ultrasound transducers enables the compact, self-contained measurement module construction. In a further embodiment, the circuitry on the first and second ASICs can be combined on a single ASIC to further reduce form factor, power, and cost.

Figure 8:
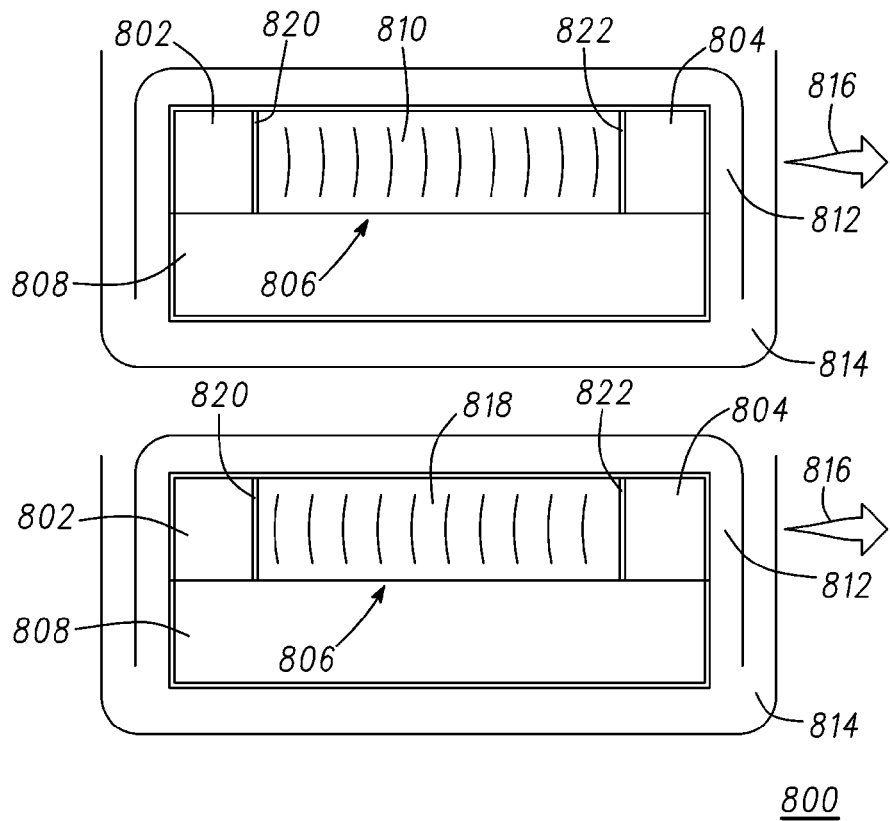
FIG. 8 is an exemplary assemblage that illustrates propagation of ultrasound waves within the waveguide in the bi-directional mode of operation of this assemblage in accordance with one embodiment.

FIG. 8 is an exemplary assemblage 800 that illustrates propagation of ultrasound waves 810 within the waveguide 806 in the bi-directional mode of operation of this assemblage. In this mode, the selection of the roles of the two individual ultrasound resonators (802, 804) or transducers affixed to interfacing material 820 and 822, if required, are periodically reversed. In the bi-directional mode the transit time of ultrasound waves propagating in either direction within the waveguide 806 can be measured. This can enable adjustment for Doppler effects in applications where the sensing module 808 is operating while in motion 816. Furthermore, this mode of operation helps assure accurate measurement of the applied load, force, pressure, or displacement by capturing data for computing adjustments to offset this external motion 816. An advantage is provided in situations wherein the body, instrument, appliance, vehicle, equipment, or other physical system 814, is itself operating or moving during sensing of load, pressure, or displacement. Similarly, the capability can also correct in situation where the body, instrument, appliance, vehicle, equipment, or other physical system, is causing the portion 812 of the body, instrument, appliance, vehicle, equipment, or other physical system being measured to be in motion 816 during sensing of load, force, pressure, or displacement. Other adjustments to the measurement for physical changes to system 814 are contemplated and can be compensated for in a similar fashion. For example, temperature of system 814 can be measured and a lookup table or equation having a relationship of temperature versus transit time can be used to normalize measurements. Differential measurement techniques can also be used to cancel many types of common factors as is known in the art.

The use of waveguide 806 enables the construction of low cost sensing modules and devices over a wide range of sizes, including highly compact sensing modules, disposable modules for bio-medical applications, and devices, using standard components and manufacturing processes. The flexibility to construct sensing modules and devices with very high levels of measurement accuracy, repeatability, and resolution that can scale over a wide range of sizes enables sensing modules and devices to the tailored to fit and collect data on the physical parameter or parameters of interest for a wide range of medical and non-medical applications.

Referring back to FIG. 2, although not explicitly illustrated, it should be noted that the load insert sensing device 100 and associated internal components move in accordance with motion of the femur 108 as shown. The bi-directional operating mode of the waveguide mitigates the Doppler effects resulting from the motion. As previously indicated, incorporating data from the accelerometer 121 with data from the other components of the sensing module 200 helps assure accurate measurement of the applied load, force, pressure, displacement, density, localized temperature, or viscosity by enabling computation of adjustments to offset this external motion.

For example, sensing modules or devices may be placed on or within, or attached or affixed to or within, a wide range of physical systems including, but not limited to instruments, appliances, vehicles, equipments, or other physical systems as well as animal and human bodies, for sensing the parameter or parameters of interest in real time without disturbing the operation of the body, instrument, appliance, vehicle, equipment, or physical system.

In addition to non-medical applications, examples of a wide range of potential medical applications may include, but are not limited to, implantable devices, modules within implantable devices, modules or devices within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment. Many physiological parameters within animal or human bodies may be measured including, but not limited to, loading within individual joints, bone density, movement, various parameters of interstitial fluids including, but not limited to, viscosity, pressure, and localized temperature with applications throughout the vascular, lymph, respiratory, and digestive systems, as well as within or affecting muscles, bones, joints, and soft tissue areas. For example, orthopedic applications may include, but are not limited to, load bearing prosthetic components, or provisional or trial prosthetic components for, but not limited to, surgical procedures for knees, hips, shoulders, elbows, wrists, ankles, and spines; any other orthopedic or musculoskeletal implant, or any combination of these.

Figure 9:
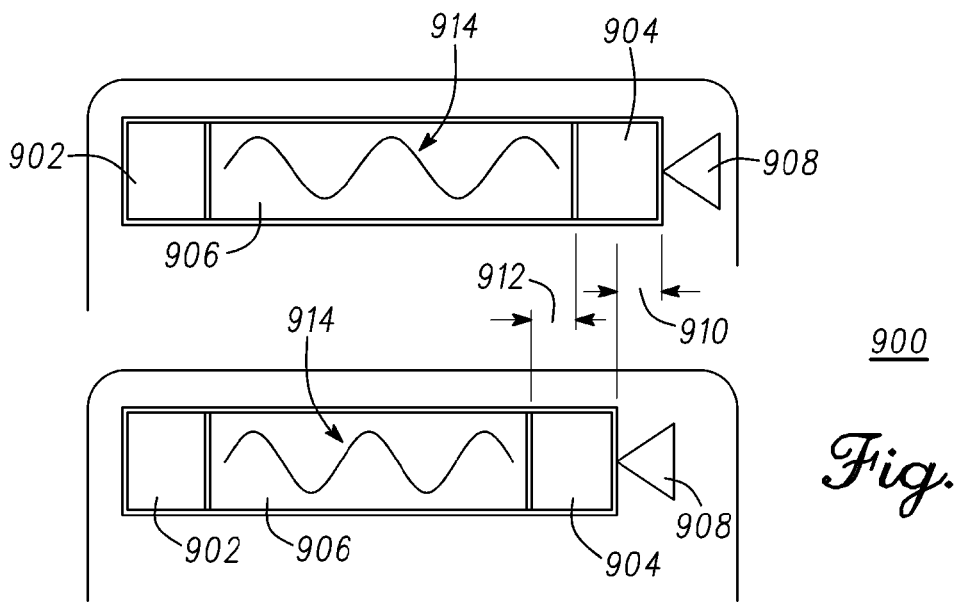
FIG. 9 is an exemplary cross-sectional view of an ultrasound waveguide to illustrate changes in the propagation of ultrasound waves with changes in the length of the waveguide in accordance with one embodiment.

FIG. 9 is an exemplary cross-sectional view of a sensor element 900 to illustrate changes in the propagation of ultrasound waves 914 with changes in the length of a waveguide 906. In general, the measurement of a parameter is achieved by relating displacement to the parameter. In one embodiment, the displacement required over the entire measurement range is measured in microns. For example, an external force 908 compresses waveguide 906 thereby changing the length of waveguide 906. Sensing circuitry (not shown) measures propagation characteristics of ultrasonic signals in the waveguide 906 to determine the change in the length of the waveguide 906. These changes in length change in direct proportion to the parameters of interest thus enabling the conversion of changes in the parameter or parameters of interest into electrical signals.

As previously discussed, external forces applied to the sensing module 200 compress the waveguide(s) thereby changing the length of the waveguide(s). The sensing module 200 measures propagation characteristics of ultrasonic signals in the waveguide(s) to determine the change in the length of the waveguide(s). These changes in length change in direct proportion to the parameters of interest thus enabling the conversion of changes in the parameter or parameters of interest into load (or force) information.

As illustrated, external force 908 compresses waveguide 906 and pushes the transducers 902 and 904 closer to one another by a distance 910. This changes the length of waveguide 906 by distance 912 of the waveguide propagation path between transducers 902 and 904. Depending on the operating mode, the sensing circuitry measures the change in length of the waveguide 906 by analyzing characteristics of the propagation of ultrasound waves within the waveguide.

One interpretation of FIG. 9 illustrates waves emitting from transducer 902 at one end of waveguide 906 and propagating to transducer 904 at the other end of the waveguide 906. The interpretation includes the effect of movement of waveguide 906 and thus the velocity of waves propagating within waveguide 906 (without changing shape or width of individual waves) and therefore the transit time between transducers 902 and 904 at each end of the waveguide. The interpretation further includes the opposite effect on waves propagating in the opposite direction and is evaluated to estimate the velocity of the waveguide and remove it by averaging the transit time of waves propagating in both directions.

Changes in the parameter or parameters of interest are measured by measuring changes in the transit time of energy pulses or waves within the propagating medium. Closed loop measurement of changes in the parameter or parameters of interest is achieved by modulating the repetition rate of energy pulses or the frequency of energy waves as a function of the propagation characteristics of the elastic energy propagating structure.

In a continuous wave mode of operation, a phase detector (not shown) evaluates the frequency and changes in the frequency of resonant ultrasonic waves in the waveguide 906. As will be described below, positive feedback closed-loop circuit operation in continuous wave (CW) mode adjusts the frequency of ultrasonic waves 914 in the waveguide 906 to maintain a same number or integer number of periods of ultrasonic waves in the waveguide 906. The CW operation persists as long as the rate of change of the length of the waveguide is not so rapid that changes of more than a quarter wavelength occur before the frequency of the propagation tuned oscillator (PTO) can respond. This restriction exemplifies one advantageous difference between the performance of a PTO and a Phase Locked Loop (PLL). Assuming the transducers are producing ultrasonic waves, for example, at 2.4 MHz, the wavelength in air, assuming a velocity of 343 microns per microsecond, is about 143 µ, although the wavelength within a waveguide may be longer than in unrestricted air.

In a pulse mode of operation, the phase detector measures a time of flight (TOF) between when an ultrasonic pulse is transmitted by transducer 902 and received at transducer 904. The time of flight determines the length of the waveguide propagating path, and accordingly reveals the change in length of the waveguide 906. In another arrangement, differential time of flight measurements (or phase differences) can be used to determine the change in length of the waveguide 906. A pulse consists of a pulse of one or more waves. The waves may have equal amplitude and frequency (square wave pulse) or they may have different amplitudes, for example, decaying amplitude (trapezoidal pulse) or some other complex waveform. The PTO is holding the phase of the leading edge of the pulses propagating through the waveguide constant. In pulse mode operation the PTO detects the leading edge of with an edge-detect receiver rather than a zero-crossing or transition as detected by a zero-crossing receiver used in CW mode.

It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light.

Figure 10:
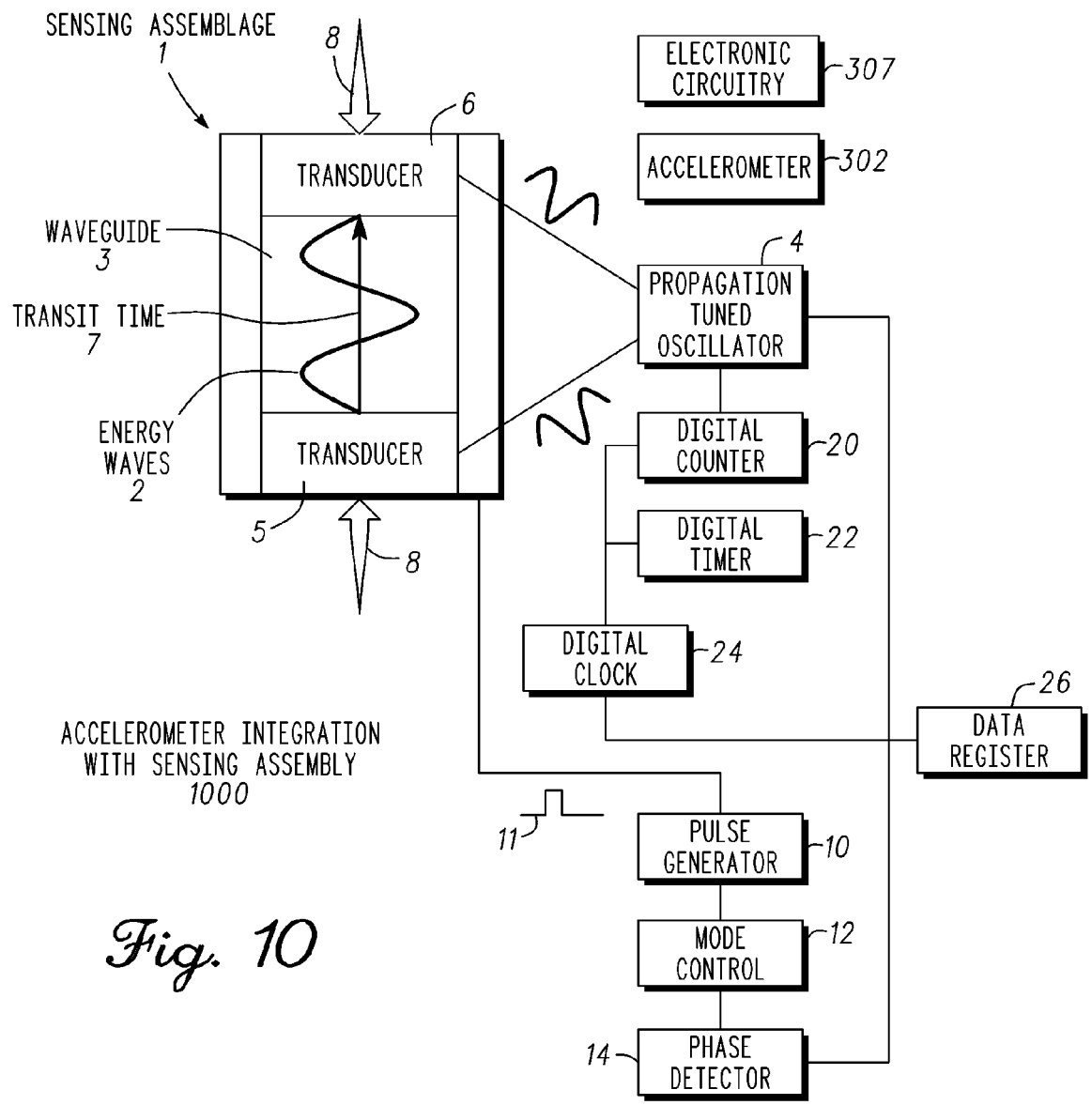
FIG. 10 is an exemplary block diagram of a propagation tuned oscillator (PTO) to maintain positive closed-loop feedback in accordance with an exemplary embodiment.

FIG. 10 is an exemplary block diagram 1000 of a propagation tuned oscillator (PTO) 4 to maintain positive closed-loop feedback in accordance with an exemplary embodiment. The measurement system includes a sensing assemblage 1 and propagation tuned oscillator (PTO) 4 that detects energy waves 2 in one or more waveguides 3 of the sensing assemblage 1. In one embodiment, energy waves 2 are ultrasound waves. A pulse 11 is generated in response to the detection of energy waves 2 to initiate a propagation of a new energy wave in waveguide 3. It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light.

Recall that the sensing insert device 100 when in motion measures forces on the sensing assemblies by evaluating propagation times of energy waves within the waveguides in conjunction with the accelerometer data. The propagation tuned oscillator (PTO) 4 measures a transit time of ultrasound waves 2 within the waveguide 3 in a closed-loop configuration. The digital counter 20 determines the physical change in the length of the waveguide. Referring to FIG. 5, the one or more accelerometers 302 determines the changes along x, y and z dimensions. The electronic circuitry 307 in view of the accelerometer data from accelerometer 302 and the physical changes in length of the sensing assemblage 1 determines the applied loading (or forces).

The sensing assemblage 1 comprises transducer 5, transducer 6, and a waveguide 3 (or energy propagating structure). In a non-limiting example, sensing assemblage 1 is affixed to load bearing or contacting surfaces 8. External forces applied to the contacting surfaces 8 compress the waveguide 3 and change the length of the waveguide 3. Under compression, transducers 5 and 6 will also be moved closer together. The change in distance affects the transit time 7 of energy waves 2 transmitted and received between transducers 5 and 6. The propagation tuned oscillator 4 in response to these physical changes will detect each energy wave sooner (e.g. shorter transit time) and initiate the propagation of new energy waves associated with the shorter transit time. As will be explained below, this is accomplished by way of PTO 4 in conjunction with the pulse generator 10, the mode control 12, and the phase detector 14.

Notably, changes in the waveguide 3 (energy propagating structure or structures) alter the propagation properties of the medium of propagation (e.g. transit time 7). The energy wave can be a continuous wave or a pulsed energy wave. A pulsed energy wave approach reduces power dissipation allowing for a temporary power source such as a battery or capacitor to power the system during the course of operation. In at least one exemplary embodiment, a continuous wave energy wave or a pulsed energy wave is provided by transducer 5 to a first surface of waveguide 3. Transducer 5 generates energy waves 2 that are coupled into waveguide 3. In a non-limiting example, transducer 5 is a piezo-electric device capable of transmitting and receiving acoustic signals in the ultrasonic frequency range.

Transducer 6 is coupled to a second surface of waveguide 3 to receive the propagated pulsed signal and generates a corresponding electrical signal. The electrical signal output by transducer 6 is coupled to phase detector 14. In general, phase detector 14 compares the timing of a selected point on the waveform of the detected energy wave with respect to the timing of the same point on the waveform of other propagated energy waves. In a first embodiment, phase detector 14 can be a zero-crossing receiver. In a second embodiment, phase detector 14 can be an edge-detect receiver. In the example where sensing assemblage 1 is compressed, the detection of the propagated energy waves 2 occurs earlier (due to the length/distance reduction of waveguide 3) than a signal prior to external forces being applied to contacting surfaces. Pulse generator 10 generates a new pulse in response to detection of the propagated energy waves 2 by phase detector 14. The new pulse is provided to transducer 5 to initiate a new energy wave sequence. Thus, each energy wave sequence is an individual event of energy wave propagation, energy wave detection, and energy wave emission that maintains energy waves 2 propagating in waveguide 3.

The transit time 7 of a propagated energy wave is the time it takes an energy wave to propagate from the first surface of waveguide 3 to the second surface. There is delay associated with each circuit described above. Typically, the total delay of the circuitry is significantly less than the propagation time of an energy wave through waveguide 3. In addition, under equilibrium conditions variations in circuit delay are minimal. Multiple pulse to pulse timings can be used to generate an average time period when change in external forces occur relatively slowly in relation to the pulsed signal propagation time such as in a physiologic or mechanical system. The digital counter 20 in conjunction with electronic components counts the number of propagated energy waves to determine a corresponding change in the length of the waveguide 3. These changes in length change in direct proportion to the external force thus enabling the conversion of changes in parameter or parameters of interest into electrical signals.

The block diagram 1000 further includes counting and timing circuitry. More specifically, the timing, counting, and clock circuitry comprises a digital counter 20, a digital timer 22, a digital clock 24, and a data register 26. The digital clock 24 provides a clock signal to digital counter 20 and digital timer 22 during a measurement sequence. The digital counter 20 is coupled to the propagation tuned oscillator 4. Digital timer 22 is coupled to data register 26. Digital timer 20, digital timer, 22, digital clock 24 and data register 26 capture transit time 7 of energy waves 2 emitted by ultrasound resonator or transducer 5, propagated through waveguide 3, and detected by or ultrasound resonator or transducer 5 or 6 depending on the mode of the measurement of the physical parameters of interest applied to surfaces 8. The operation of the timing and counting circuitry is disclosed in more detail hereinbelow.

The measurement data can be analyzed to achieve accurate, repeatable, high precision and high resolution measurements. This method enables the setting of the level of precision or resolution of captured data to optimize trade-offs between measurement resolution versus frequency, including the bandwidth of the sensing and data processing operations, thus enabling a sensing module or device to operate at its optimal operating point without compromising resolution of the measurements. This is achieved by the accumulation of multiple cycles of excitation and transit time instead of averaging transit time of multiple individual excitation and transit cycles. The result is accurate, repeatable, high precision and high resolution measurements of parameters of interest in physical systems.

In at least one exemplary embodiment, propagation tuned oscillator 4 in conjunction with one or more sensing assemblages 1 are used to take measurements on a muscular-skeletal system. In a non-limiting example, sensing assemblage 1 is placed between a femoral prosthetic component and tibial prosthetic component to provide measured load information that aids in the installation of an artificial knee joint. Sensing assemblage 1 can also be a permanent component or a muscular-skeletal joint or artificial muscular-skeletal joint to monitor joint function. The measurements can be made in extension and in flexion. In the example, assemblage 1 is used to measure the condyle loading to determine if it falls within a predetermined range and location. Based on the measurement, the surgeon can select the thickness of the insert such that the measured loading and incidence with the final insert in place will fall within the predetermined range. Soft tissue tensioning can be used by a surgeon to further optimize the force or pressure. Similarly, two assemblages 1 can be used to measure both condyles simultaneously or multiplexed. The difference in loading (e.g. balance) between condyles can be measured. Soft tissue tensioning can be used to reduce the force on the condyle having the higher measured loading to reduce the measured pressure difference between condyles.

One method of operation holds the number of energy waves propagating through waveguide 3 as a constant integer number. A time period of an energy wave corresponds to energy wave periodicity. A stable time period is one in which the time period changes very little over a number of energy waves. This occurs when conditions that affect sensing assemblage 1 stay consistent or constant. Holding the number of energy waves propagating through waveguide 3 to an integer number is a constraint that forces a change in the time between pulses when the length of waveguide 3 changes. The resulting change in time period of each energy wave corresponds to a change in aggregate energy wave time period that is captured using digital counter 20 as a measurement of changes in external forces or conditions applied to contacting surfaces 8.

A further method of operation according to one embodiment is described hereinbelow for energy waves 2 propagating from transducer 5 and received by transducer 6. In at least one exemplary embodiment, energy waves 2 is an ultrasonic energy wave. Transducers 5 and 6 are piezo-electric resonator transducers. Although not described, wave propagation can occur in the opposite direction being initiated by transducer 6 and received by transducer 5. Furthermore, detecting ultrasound resonator transducer 6 can be a separate ultrasound resonator as shown or transducer 5 can be used solely depending on the selected mode of propagation (e.g. reflective sensing). Changes in external forces or conditions applied to contacting surfaces 8 affect the propagation characteristics of waveguide 3 and alter transit time 7. As mentioned previously, propagation tuned oscillator 4 holds constant an integer number of energy waves 2 propagating through waveguide 3 (e.g. an integer number of pulsed energy wave time periods) thereby controlling the repetition rate. As noted above, once PTO 4 stabilizes, the digital counter 20 digitizes the repetition rate of pulsed energy waves, for example, by way of edge-detection, as will be explained hereinbelow in more detail.

In an alternate embodiment, the repetition rate of pulsed energy waves 2 emitted by transducer 5 can be controlled by pulse generator 10. The operation remains similar where the parameter to be measured corresponds to the measurement of the transit time 7 of pulsed energy waves 2 within waveguide 3. It should be noted that an individual ultrasonic pulse can comprise one or more energy waves with a damping wave shape. The energy wave shape is determined by the electrical and mechanical parameters of pulse generator 10, interface material or materials, where required, and ultrasound resonator or transducer 5. The frequency of the energy waves within individual pulses is determined by the response of the emitting ultrasound resonator 4 to excitation by an electrical pulse 11. The mode of the propagation of the pulsed energy waves 2 through waveguide 3 is controlled by mode control circuitry 12 (e.g., reflectance or uni-directional). The detecting ultrasound resonator or transducer may either be a separate ultrasound resonator or transducer 6 or the emitting resonator or transducer 5 depending on the selected mode of propagation (reflectance or unidirectional).

In general, accurate measurement of physical parameters is achieved at an equilibrium point having the property that an integer number of pulses are propagating through the energy propagating structure at any point in time. Measurement of changes in the "time-of-flight" or transit time of ultrasound energy waves within a waveguide of known length can be achieved by modulating the repetition rate of the ultrasound energy waves as a function of changes in distance or velocity through the medium of propagation, or a combination of changes in distance and velocity, caused by changes in the parameter or parameters of interest.

It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light. Furthermore, the velocity of ultrasound waves within a medium may be higher than in air. With the present dimensions of the initial embodiment of a propagation tuned oscillator the waveguide is approximately three wavelengths long at the frequency of operation.

Measurement by propagation tuned oscillator 4 and sensing assemblage 1 enables high sensitivity and high signal-to-noise ratio. The time-based measurements are largely insensitive to most sources of error that may influence voltage or current driven sensing methods and devices. The resulting changes in the transit time of operation correspond to frequency, which can be measured rapidly, and with high resolution. This achieves the required measurement accuracy and precision thus capturing changes in the physical parameters of interest and enabling analysis of their dynamic and static behavior.

These measurements may be implemented with an integrated wireless sensing module or device having an encapsulating structure that supports sensors and load bearing or contacting surfaces and an electronic assemblage that integrates a power supply, sensing elements, energy transducer or transducers and elastic energy propagating structure or structures, biasing spring or springs or other form of elastic members, an accelerometer, antennas and electronic circuitry that processes measurement data as well as controls all operations of ultrasound generation, propagation, and detection and wireless communications. The electronics assemblage also supports testability and calibration features that assure the quality, accuracy, and reliability of the completed wireless sensing module or device.

In general, measurement of the changes in the physical length of individual waveguides can be made in several modes. Each assemblage of one or two ultrasound resonators or transducers combined with a waveguide can be controlled to operate in six different modes. This includes two wave shape modes: continuous wave or pulsed waves, and three propagation modes: reflectance, unidirectional, and bi-directional propagation of the ultrasound wave. In all modes of operation the changes in transit time within the ultrasound waveguides change the operating frequency of the propagation tuned oscillator 4 or oscillators. These changes in the frequency of oscillation of the propagation tuned oscillator or oscillators can be measured rapidly and with high resolution. This achieves the required measurement accuracy and precision thus enabling the capture of changes in the physical parameters of interest and enabling analysis of the dynamic and static behavior of the physical system or body.

The level of accuracy and resolution achieved by the integration of energy transducers and an energy propagating structure or structures coupled with the electronic components of the propagation tuned oscillator enables the construction of, but is not limited to, compact ultra low power modules or devices for monitoring or measuring the parameters of interest. The flexibility to construct sensing modules or devices over a wide range of sizes enables sensing modules to be tailored to fit a wide range of applications such that the sensing module or device may be engaged with, or placed, attached, or affixed to, on, or within a body, instrument, appliance, vehicle, equipment, or other physical system and monitor or collect data on physical parameters of interest without disturbing the operation of the body, instrument, appliance, vehicle, equipment, or physical system.

Figure 11:
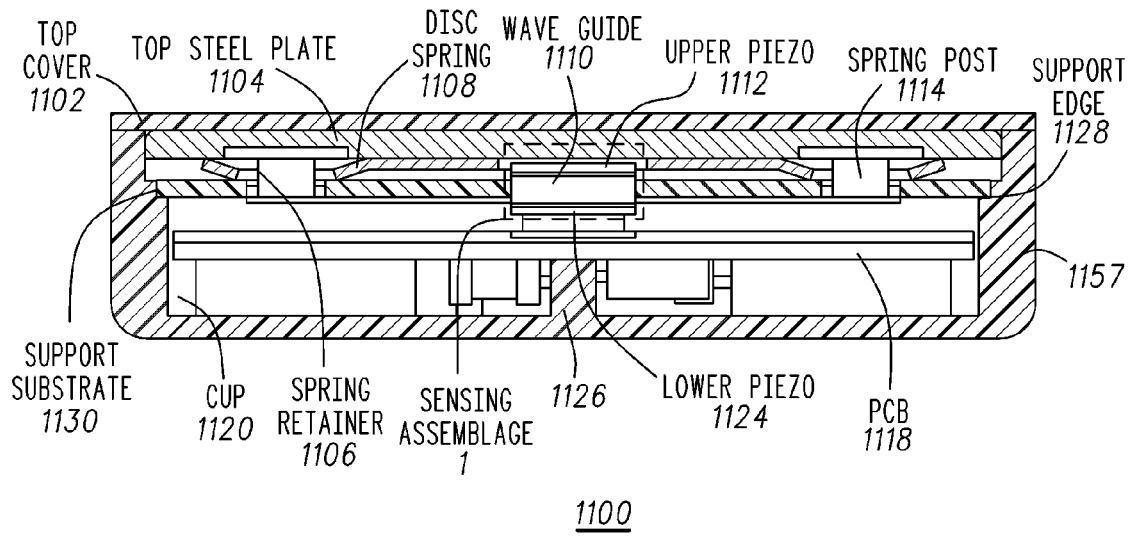
FIG. 11 is a cross-sectional view of a layout architecture of the sensing module in accordance with an exemplary embodiment.

FIG. 11 is a cross-sectional view of a layout architecture of the sensing module 200 in accordance with an exemplary embodiment. The blocks are operatively coupled within the encapsulated enclosure of the sensing module 200 and together form an encapsulated force sensor 1100. It comprises a top steel plate 1104 coupled to a lower printed circuit board (PCB) 1118 by way of spring retainer 1106, disc spring 1108, and spring post 1114. The force sensor 1100 is biased with springs or other means of elastic support to accurately maintain a required distance between the load bearing or contact surfaces such as top cover 1102 and to minimize hysteresis due to material properties of waveguide 1110.

The encapsulating force sensor 1100 supports and protects the specialized mechanical and electronic components from external physical, mechanical, chemical, and electrical, and electromagnetic intrusion that might compromise sensing or communication operations of the module or device. The encapsulating force sensor 1100 also supports internal mechanical and electronic components and minimizes adverse physical, mechanical, electrical, and ultrasonic interactions that might compromise sensing or communication operations of the module or device. Top cover 1102 and unitary main body 1157 form the encapsulating enclosure. Unitary main body 1157 is a metal, plastic, or polymer body having sufficient strength and rigidity to withstand forces, pressures, and loads of the muscular-skeletal system. In particular, the sidewalls or bottom surface do not deform under normal operating conditions. For example, the unitary main body 1157 can be formed of polycarbonate or other biocompatible material. Moreover, unitary main body 1157 can be molded in a manufacturing process that allows detailed features to be repeatably and reliably manufactured.

The physical layout architecture of sensor 1100 has the one or more sensing assemblages overlying the electronic circuitry. A force, pressure, or load is applied to a surface of sensor 1100. The surface of sensor 1100 corresponds to top steel plate 1104. Steel plate 1104 moves in response to a force, pressure, or load. The steel plate 1104 can support the movement while maintaining a seal with unitary main body 1157 that isolates an interior of the enclosure. In general, a sensing assemblage is coupled between steel plate 1104 and a substrate 1130. Substrate 1130 is a rigid non-moveable substrate that is supported by the sidewalls of unitary main body 1157. A periphery of substrate 1130 is in contact with and supported by a support feature 1128 formed in the sidewalls of unitary main body 1157. Substrate 1130 does not flex under loading. The sensing assemblage translates a displacement due to the force, pressure, or load applied to steel plate 1104 to a signal. The signal is processed by electronic circuitry in the enclosure to generate data corresponding to the force, pressure, or load value. As shown, the sensing assemblage comprises upper piezo 1112, waveguide 1110, and lower piezo 1124. Upper piezo 1112 and lower piezo 1124 are ultrasonic piezo-electric transducers.

Electronic circuitry to power, control, interface, operate, measure, and send sensor data is interconnected together on a printed circuit board (PCB) 1118. One or more cups 1120 are formed in unitary main body 1157. In one embodiment, the components mounted on PCB 1118 reside within cups 1120. One or more structures 1126 support and fix the position of the PCB 1118. The components on PCB 1118 are suspended in the cups 1120 and do not have contact with unitary main body 1157 thereby preventing interconnect stress that could result in long-term reliability issues. The PCB 1118 is mechanically isolated from substrate 1130. Thus, any force, pressure, or loading on substrate 1130 is not applied to PCB 1118. Flexible interconnect is used to connect from the electronic circuitry on PCB 1118 to upper piezo 1112 and lower piezo 1124.

In one embodiment, more than one sensing assemblage couples to predetermined locations of the steel plate 1104. Each sensing assemblage can measure a parameter applied to steel plate 1104. In combination, the sensing assemblages can determine a location or region where the parameter is applied to the surface. For example, the magnitude and position of the loading on the contacting surface of sensing module 200 applied by femur 102 and tibia 108 to sensing module 200 can be measured and displayed as shown in FIG. 2. In a non-limiting example, three sensing assemblages can be spaced on a periphery of steel plate 1104. In the example, each sensing assemblage will measure a force applied to steel plate 1104. The location of the applied force is closest to the sensing assemblage detecting the highest force magnitude. Conversely, the sensing assemblage detecting the weakest force magnitude is farthest from the applied force. The measured force magnitudes in combination with the predetermined locations where the sensing assemblages couple to steel plate 1104 can be used to determine a location where the parameter is applied.

The housing electrically insulates the internal electronic, sensing, and communication components. The encapsulating force sensor 1100 eliminates parasitic paths that might conduct ultrasonic energy and compromise excitation and detection of ultrasound waves within the sensing assemblages during sensing operations. A temporary bi-directional electrical interconnect assures a high level of electrical observation and controllability of the electronic assembly within the encapsulating force sensor 1100. The temporary interconnect also provides a high level of electrical observation of the sensing subsystem, including the transducers, waveguides, and mechanical spring or elastic assembly.

Ultrasound waveguide 1110 is coupled to the top cover 1102. A force applied to the top cover 1102 compresses waveguide 1110. Lower piezo 1124 and upper piezo 1112 are piezo-electric transducers respectively coupled to waveguide 1110 at a first and second location. Waveguide 1110 is a compressible propagation medium for ultrasonic energy waves. The transducers emit energy waves and detect propagated energy waves in waveguide 1110. Electronic circuitry is coupled to lower piezo 1124 and upper piezo 1112 to measure transit time, frequency, or phase of the propagated energy waves. The transit time, frequency, or phase of energy waves propagating between the first and second locations of waveguide 1110 can be precisely measured and therefore the length of the ultrasound waveguide 1110. The length of waveguide 1110 is calculated by a known function relating material properties of the waveguide 1110 to the parameter being measured. In the example, a force, pressure, or load is calculated from the measured length of waveguide 1110.

The encapsulated force sensor 1100 can accurately and repeatably measure one pound changes in load with changes in length of a waveguide comprising 2.5 microns. The maximum change in the present implementation is specified at less than 5.0 microns. This assures that the size of the sensing module 200 throughout all measurements remains within the required dimension (e.g., distance) of the insert between the load bearing surfaces of the prosthetic components.

An exemplary level of control of the compression or displacement of the waveguides 1110 with changes in load, force, pressure, or displacement is achieved by positioning the spring or springs 1108 or other means of elastic support, including the waveguides 1110 themselves, between the load bearing contact surfaces to minimize any tendency of the load bearing contact surfaces to cantilever. Cantilevering can compromise the accuracy of the inclination of the load bearing contact surface whenever load, force, pressure, or displacement is applied to any point near a periphery of the load bearing contact surfaces. In one embodiment, springs 1108 are disc springs. The spring 1108 is held in a predetermined location by spring post 1114 and spring retainer 1104.

The walls of the unitary main body 1157 include a small gap to enable the steel plate 1104 to move. The hermetic seal is also flexible to allow the steel plate 1104 of the force sensor 1104 to slide up and down, like a piston, for distances on the order of a hundred microns without compromising integrity of the seal. The hermetic seal completes manufacturing, sterilization, and packaging processes without compromising ability to meet regulatory requirements for hermeticity. The level of hermeticity is sufficient to assure functionality and biocompatibility over the lifetime of the device. Implant devices with total implant time less than 24 hours may have less stringent regulatory requirements for hermeticity. Unbiased electrical circuitry is less susceptible to damage from moisture. The electronics in one embodiment are only powered during actual usage. In another embodiment, the encapsulated force sensor 1100 employs low duty cycles to serve as a measurement-on-demand device to efficiently perform at low total operating time when the electronics are powered on.

The encapsulating force sensor 1100 has a compact size permitting it to fit for example within a trial insert, final insert, prosthetic component, tool, equipment, or implant structure to measure the level and incidence of the load on subsequent implanted prosthetic devices. It can be constructed using standard components and manufacturing processes. Manufacturing carriers or fixtures can be designed to emulate the final encapsulating enclosure of the sensing module 200. Calibration data can be obtained during the manufacturing processing thus enabling capture of accurate calibration data. These calibration parameters can be stored within the memory circuits integrated into the electronics assemblage of the sensing module 200. Testability and calibration further assures the quality and reliability of the encapsulated enclosure.

Examples of a wide range of potential medical applications can include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

Figure 12:
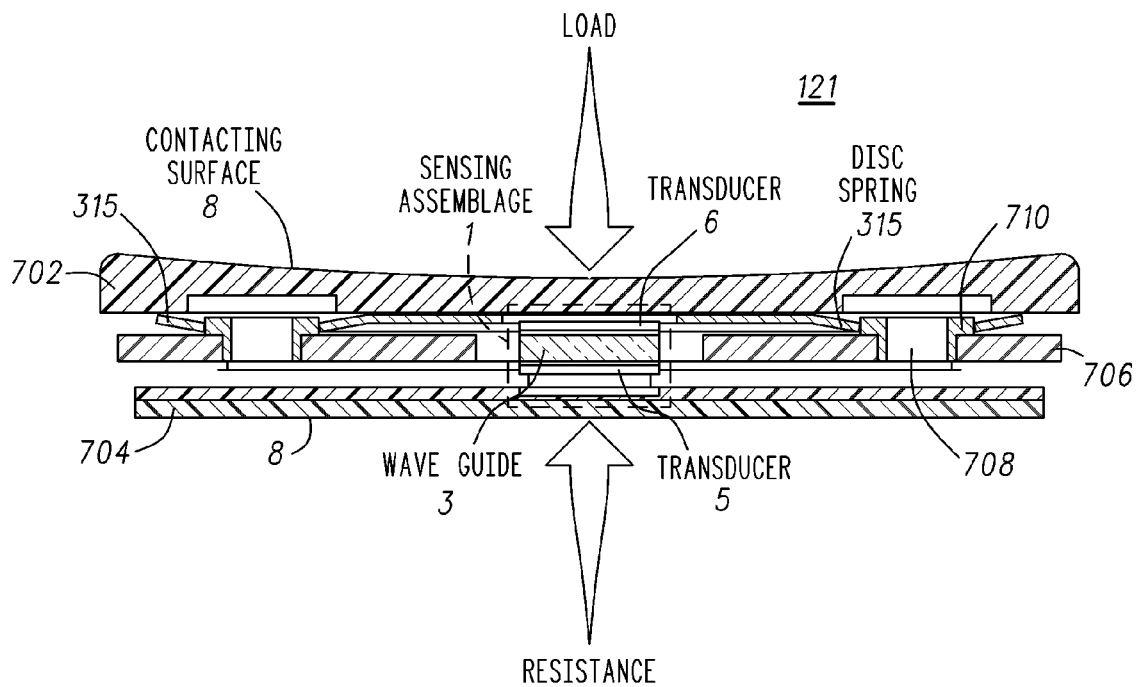
FIG. 12 is a simplified cross-sectional view of an embodiment of the load sensing platform in accordance with an exemplary embodiment.

FIG. 12 is a simplified cross-sectional view of an embodiment of the load sensing platform 121 in accordance with an exemplary embodiment. The load sensing platform 121 is placed, engaged, attached, or affixed to or within a physical system with a portion of the system contacting the load bearing or contacting surfaces of the load sensing platform 121. As disclosed in FIG. 1 the load sensing platform 121 can be used intra-operatively to measure parameters of the muscular-skeletal system during joint replacement surgery. In the example, the load bearing platform 121 is placed in a joint of the muscular-skeletal system to measure force, pressure, or load and the location where the force, pressure, or load is applied. The lower load bearing surface 8 contacts the tibial component 106 of the artificial knee. The upper load bearing surface 8 contacts the femoral component 104 of the artificial knee. Not shown are the muscles, ligaments, and tendons of the muscular-skeletal system that apply a compressive force, pressure, or load on the surfaces 8 of the load sensing platform 121. The load sensing platform 121 has a form factor that allows integration in tools, equipment, and implants. The load sensing platform 121 is bio-compatible and can be placed in an implant or attached to the muscular-skeletal system to provide long term monitoring capability of natural structures or artificial components.

A compact sensing platform is miniaturized to be placed on or within a body, instrument, appliance, vehicle, equipment, or other physical system without disturbing the operation of the body, instrument, appliance, vehicle, equipment, or physical system. This facilitates contacting the sources of load, force, pressure, displacement, density, viscosity, or localized temperature to be measured. The non-limiting example of load sensing platform 121 can include circuitry disclosed in FIG. 5. Two or more springs or other means of elastic support 315 support the load bearing or contacting surfaces 8. One or more assemblages each comprised of one or two ultrasound resonators or transducers are coupled between load bearing surfaces 8.

As shown, a single sensing assemblage 1 is centrally located in load sensing platform 121. Sensing assemblage 1 is a stack comprising the upper transducer 6, the lower transducer 5, and the waveguide 3. In one embodiment, the waveguide 3 is cylindrical in shape having a first end and a second end. Transducers 5 and 6 respectively overlie the first and second ends of waveguide 3. An interface material can be used to attach and enhance acoustical coupling between a transducer and waveguide. The stack is positioned in contact with, attached, or coupled to the load bearing or contacting surfaces 8. Electrical interconnect such as a flex interconnect couples to terminals of transducers 5 and 6. The flex interconnect (not shown) electrically connects transducers 5 and 6 to electronic circuitry 307 of the sensing module 200.

The upper load bearing surface 8 is a surface of an upper substrate 702. An interior surface of the upper substrate 702 couples to transducer 6. Similarly, the lower load bearing surface 8 is a surface of a lower substrate 704. An interior surface of the lower substrate couples to the transducer 5. A load, force, or pressure applied across load bearing surfaces 8 can compress or lengthen waveguide 3. This arrangement facilitates translating changes in the parameter or parameters of interest into changes in the length or compression of the waveguide or waveguides 3 and converting these changes in the length or compression of the waveguide 3 or waveguides into electrical signals by way of transducers 5 or 6 thus enabling sensing assemblage 1 to sense changes in the physical parameters of interest with minimal disturbance to the operation of the external body, instrument, appliance, vehicle, equipment, or physical system. To achieve the required level of miniaturization, the length of the ultrasound waveguides 3 is on the order of 10 millimeters in length. The measurable resolution of compression or displacement of waveguide is on the order of sub-microns.

One or more springs 315 or other means of elastic support, support the load bearing or contacting surfaces 8. The one or more springs control a compression of load sensing platform 121. For example, waveguide 3 can comprise a polymer material suitable for energy wave propagation. In one embodiment, the polymer material changes dimension when a parameter to be measured is applied to waveguide 3. A relationship is known between the polymer material and a measured dimension. Changes in dimension are measured and the parameter calculated by way of the known relationship. The polymer material can exhibit mechanical hysteresis whereby the material in-elastically responds to changes in the applied parameter. In the example, the length of waveguide 3 responds to the force, pressure, or load applied across contacting surfaces 8. Moreover, the polymer material may not rebound in a timely fashion as the force, pressure or load changes. Springs 315 aid in the transition as waveguide 3 responds to different levels of compression. Springs 315 bring the load sensing platform 121 to an accurate and repeatable quiescent state or condition. Springs further prevent the cantilevering of load bearing surfaces 8 that can reduce an accuracy of measurement. Cantilevering becomes more prevalent as forces, pressures, and loads are applied towards the periphery of a contact area of load bearing surfaces 8.

In one embodiment, the springs 315 that support load bearing surfaces 8 are disc springs or a wave springs. Disc springs are capable of maintaining waveguide 3 at a precise length. The compression of the waveguide 3 is very accurate over the measurement range. The compression of the disc springs can be monotonic over the range of applied levels of force, pressure, or load. In one embodiment, the surfaces of the disc springs are polished to assure smooth compression with changes in force applied to contact surfaces 8. A further benefit of the disk springs is that they eliminate or minimize cantilevering of the load supporting substrate that can compromise the accuracy due to the inclination of load bearing surfaces 8. In the illustration, two springs 315 are shown that are located on the periphery of load sensing platform 121. Although not shown, other springs 315 may reside in the load sensing platform 121 at other predetermined locations. Typically, the contact area where the parameter is applied to load bearing surfaces 8 is within an area bounded by springs 315.

In one embodiment, a substrate 706 is resides between upper substrate 702 and lower substrate 704. Sensing assemblage 1 couples through an opening in substrate 706 to couple to the interior surfaces of substrates 702 and 704 to measure a force, pressure, or load applied across load bearing surfaces 8. In the example, substrate 702 moves as a force, pressure, or load is applied while substrate 704 remains in a fixed position.

Thus, a force, pressure, or load applied to contacting surface 8 changes a distance between substrates 702 and 704 and therefore the length of waveguide 3. Substrates 704 and 706 are planar to one another separated by a predetermined spacing. Substrates 704 and 706 remain in the fixed relation to one another under loading.

Springs 315 are placed between an upper surface of substrate 706 and the interior surface of substrate 702. As disclosed in the example, springs 315 are disc springs. The disc springs are concave in shape. The disc spring is formed having a centrally located circular opening. The surface of springs 315 proximally located to the circular opening contacts the upper surface of substrate 706. The surface of springs 315 proximally located to the outer edge of springs 315 contacts the interior surface of substrate 702. A force applied across the load bearing surface 8 of load sensing platform 121 will compress springs 315 and waveguide 3. The amount of compression of waveguide 3 over a measurable range can be very small but will provide precision accuracy of the parameter. For example, waveguide 3 may be compressed less than a millimeter for a force measurement ranging from 5 to 100 lbs. In the example, the length of waveguide 3 is precisely measured using acoustic energy wave propagation. The measured length is then converted to the force, pressure, or load. The springs 315 support movement of the waveguide 3 upon a change in force, pressure, or loading. For example, springs 315 repeatably return the load sensing platform 121 to a precise quiescent state upon releasing an applied force. The characteristics of springs 315 are known over the measurement range of load sensing platform 121. The calculated measured value of the parameter can include compensation due to springs 315.

Spring 315 are in a fixed location in load sensing platform 121. The disc springs are located on the periphery of the load sensing platform 121. Spring posts 708 and spring retainers 710 are used to align and fix springs 315 in each predetermined location. Spring post 708 aligns substrate 702 to substrate 706. Spring post 708 and spring retainer 710 aligns to corresponding openings in substrate 706. In one embodiment, a cap of post 708 fits into a corresponding cavity of the interior surface of substrate 702. Spring retainer 710 is a sleeve that overlies post 708. Post 708 and spring retainer 710 couples through a corresponding opening in substrate 706. Spring retainer 710 has a lip that overlies and contacts the upper surface of substrate 706. The spring post 708 and spring retainer 710 couple through the opening in the disc spring. The edge of the opening rests against the edge of the lip of retainer 710 thereby retaining and holding spring 315 in the predetermined location. Spring 315 can move vertically allowing waveguide 3 to change length due to the parameter being applied to contact surfaces 8.

In one embodiment, load sensing platform 121 can locate a position where the parameter is applied on a load bearing surface. Locating the position can be achieved by using more than one sensing assemblages 1. In one embodiment, three sensing assemblages 1 couple to load bearing or contacting surface 8 at three predetermined locations. The parameter is measured by each sensing assemblages 1. The magnitudes of each measurement and the differences between measurements of the sensing assemblages 1 are compared. For example, the location of the applied parameter is closer to the sensing assemblage that generates the highest reading. Conversely, the location of the applied parameter will be furthest from the sensing assemblage that generates the lowest reading. The exact location can be determined by comparison of the measured values of each sensing assemblage in conjunction with knowledge of the predetermined locations where each assemblage contacts load bearing or contacting surface 8.

FIG. 14 is an exemplary block diagram schematic of a compact low-power energy source 1400 integrated into an exemplary electronic assembly of the sensing module 200 in accordance with one embodiment. The schematic illustrates one embodiment of the capacitive energy storage 1400 having an induction coupling to an external power source 1402 to transfer energy to a super capacitor or capacitor as an energy storage device that provides operating power for sensing module 200. The compact low-power energy source 1400 can comprise an induction coil 1404, a rectifier 1406, a regulator 1408, a capacitive energy storage device 1410, a power management circuit 1412, and operational circuitry 1414. The latter circuits can be analog or discrete components, assembled in part or whole with other electronic circuitry, custom designed as an ASIC, or any combination thereof.

The external energy source 1402 can be coupled to a battery or batteries or an alternating current power supply. For example, external energy source 1402 can be an external hand-held device with its own battery that wirelessly transfers charge from the battery of the hand-held device to the energy source 1400 of the sensing device. The surgeon or technician can hold the hand-held device in close proximity to the sensing device prior to or during orthopedic surgery to provide sufficient charge to operate the device during the procedure. The sensing device as a long-term implant can be charged by the patient at his or her own convenience to initiate a measurement process that provides information on the implant status. In other embodiments, the sensing module 200 being powered by charge from external energy source 1402 can communicate a signal to indicate a recharging operation is necessary, for example, when in the proximity of a charging device.

External energy source 1402 can be coupled wirelessly to capacitive energy storage device 1410 through electromagnetic induction coil or coils 1404, rectifier 1406 and regulator 1408. The charging operation is controlled by power management circuitry 1412. During operation of operating circuitry 1414, power is transferred from capacitive energy storage device 1410 by power management circuitry 1412 that includes, but is not limited to, efficient step-up and step-down voltage converter circuitry that conserves operating power of circuit blocks at the minimum voltage levels that support the required level of performance. Clock frequencies are also optimized for performance, power, and size to assure digital circuit blocks operate at the optimum clock rates that support the required level of performance. Circuit components are partitioned among integrated circuits and discrete components to minimize power consumption without compromising performance. Partitioning functions between digital and analog circuit also enhances design flexibility and facilitates minimizing power consumption without sacrificing functionality or performance.

A method of powering and operation of the sensing module is disclosed below. The method can be practiced with more or less than the number of steps shown and is not limited to the order shown. To describe the method, reference will be made to the components of other figures described hereinabove although it is understood that the method can be implemented in any other manner using other suitable components. The sensing module 200 described in FIG. 5 including capacitive energy storage capability and highly efficient, low power operating performance can be used to illustrate the operating principles of the method. The method is initiated when the external power source 1402 begins transmitting power within range of the induction coil or coils 1404 of the sensing module 200. In a second step, the induction coils 1404 are coupled to the electromagnetic waves such that the electromagnetic waves are sensed. The induction coil or coils 1404 are energized by the power transmissions from external power source 1402. In a third step, the coupled electromagnetic waves create an AC voltage signal in induction coil or coils 1404. In a fourth step, the rectifier 1406 rectifies the AC voltage signal to produce a rectified voltage signal. In one embodiment, the voltage level across induction coil or coils 1404 rises to a level that a rectified signal is generated by full-wave rectifier 1406. In a fifth step, the rectified voltage signal is used to charge the capacitive energy storage device 1410, which holds the charge. In a non-limiting example, the energy storage device 1410 is a super capacitor or capacitor having a small form factor with enough storage capability to power the sensing module 200 for a predetermined period of time. In a sixth step, the voltage regulator 1408 ensures that the capacitive energy storage device 1410 is charged to, and maintains a voltage level that is greater than the required operating voltage of the sensing module 200. In a seventh step, the power management circuitry 1412 monitors the level of charge on capacitive energy storage device 1410 to determine if the voltage exceeds a threshold. The threshold can correspond to a shunt threshold established by the regulator 1408. The operating electronics circuitry 1414 is enabled when it is determined in that an adequate level of charge has been stored to power the sensing module 200 for at least the predetermined time period.

In an eighth step, the power management circuitry 1412 disconnects the energy storage device 1410 from the charging circuitry (1404, 1406, and 1408) when the coupling with external power source 1402 is removed or terminated. Power management circuitry 1412 continues to monitor the level of charge on capacitive energy storage device 1410. The power management circuitry 1412 powers down the sensing module 200 including the operational circuitry 1414 when the charge or voltage level falls below a predetermined threshold. The power management circuitry 1412 subsequently discharges remaining charge on the energy storage device 1410 to prevent unreliable, intermittent, or erratic operation of the operational circuitry 1414.

Under nominal conditions, a charge time from zero charge to fully charged is approximately 3 minutes. In one embodiment, the maximum charge time is specified to be no greater than 7 minutes. The charging time of a capacitor powered system is a major improvement over the two hours or more required to fully charge a battery from zero charge regardless of battery capacity. The capacitive energy storage device 1410 can include capacitors with solid dielectrics that have longer lifetimes than batteries, can be left uncharged, and will not degrade regardless of length of time at a zero charge. In one arrangement, the wireless charging operation can be performed by electromagnetic induction before removal of any sterile packaging. The capacitive energy storage device 1410 is applicable for powering chronic active implantable devices where data collection is discrete point-of-time measurements rather than continuous, fulltime data collection and storage.

The compact low-power energy source can be used as a backup power source for sensing module 200 should the primary power source be terminated. A method performed by the compact low-power energy source as a backup power source is disclosed below. The method can be practiced with more or less than the number of steps shown and is not limited to the order shown. To describe the method, reference will be made to the components of FIGS. 1, 5 and 14, although it is understood that the method can be implemented in any other manner using other suitable components. The medical sensing device 100 described in FIG. 1 including capacitive energy storage capability and highly efficient, low power operating performance can be used to illustrate the operating principles of method as a back-up power source. Broadly stated, the method is directed to charging the sensing insert device 100 by way of a wired connection instead of wireless induction charging.

In a first step, the induction coil 1404 is electrically decoupled. In a second step, the rectifier 1406 and the regulator 1408 are disabled. At this juncture, the method enters a state where capacitive energy storage device 1410 is decoupled from the wireless charging circuits; that is, the power transmission components inductor 1404, rectifier 1406, and regulator 1408 are disabled. As one example, an electrical switching operation disengages the connection upon the power management circuitry 1412 detecting a direct line charge on the capacitive energy storage device 1410. In another arrangement, the power management circuitry 1412 further checks whether the induction coils are energized at the time of the applied line charge, thereby indicating that the energy is being delivered via a wired connection instead, since no induction activity by an external power source 1402 is detected.

In a second step, the wired energy source starts and charges capacitive energy storage device 1410. The wired energy source maintains capacitive energy storage device 1410 at full charge under normal operating conditions through direct electrical coupling. Power management circuitry 1412 monitors the level of charge on capacitive energy storage device 1410. If at a third step, power from wired energy source is interrupted, power management circuitry 1412 isolates the capacitive energy storage device 1410 from the wired energy source. As one example, a power interruption occurs when an individual manually disconnects the wired power source from the sensing module 200. This could also occur in response to an energy spike or power drop in the wired energy source. As another example, a power interruption could occur upon the power management circuitry 1412 detecting the presence of an external power source 1402 attempting to charge the sensing module 200 and thereby competing with the wired energy source.

In a fourth step, the power management circuitry 1412 can commence to supply the energy stored on the capacitive energy storage device 1410 to operating circuitry 1414 and associated electronics for normal operation. In a fifth step, power management circuitry 1412 monitors the level of charge on capacitive energy storage device 1410. In a sixth step, the power management circuitry 1412 will allow the continued supply of energy to the operating circuitry 1414 as long as the voltage on capacitor 1410 exceeds a voltage threshold. In a seventh step, the power management circuitry 1412 powers down the electronic assembly when the charge or voltage level falls below the predetermined charge of voltage threshold. The threshold is chosen to provide sufficient time to power down the operational circuitry 1414 in an orderly fashion.

If the wired energy source is restored, power management circuitry 1412 resumes the direct connection of power between the wired energy source and operational circuitry 1414. Power management circuitry 1412 also resumes the coupling of power between the wired energy source and capacitive energy storage device 1410 and resumes maintaining it at full charge.

FIG. 15 is an exemplary flow chart of a method 1500 for wireless power modulation telemetry in accordance with one embodiment. The method 1500 can be practiced with more or less than the number of steps shown and is not limited to the order shown. To describe the method 1500, reference will be made to the components of FIGS. 1, 5 and 14, although it is understood that the method 1500 can be implemented in any other manner using other suitable components.

In a step 1502, the external wireless energy source 125 acquires input data. As one example, the user can manually enter the input data via a touchscreen or a user interface menu on the external wireless energy source 125. In another arrangement, the input data in response to a user directive can be communicatively uploaded to the external wireless energy source 125, for example, by USB or via a wi-fi connection. The input data can be information such as a serial number, a registration code, biasing parameters (e.g., spring constants, load balancing), updated parameters, version control information, security code information, data log tags, operational control information, or any other data. More specifically, data and instructions to be transmitted to the sensing insert device 100 is input into a data input port 128 of external wireless energy source 125.

As one example, referring back briefly to FIG. 1, the receiver station 110 can query a serial number from the sensing insert device 100 for updating medical records and inventory. Sensing insert device 100 includes the sensing module 200. As another example, the external wireless energy source 125 can download an operation code for adjusting a bias level of one of the springs in the sensing assemblies 303, or establishing an operating mode (e.g., standby, debug, flash). Following the acquisition of input data, the external wireless energy source 125 can be placed in the proximity of the load insert sensing device 100. At this point, operation of an external charging device or wireless energy source 1402 is initiated and contact is established with insert sensing device 100.

In a step 1504, the external wireless energy source 125 proceeds with secure encoding of the input data. As one example, the external wireless energy source 125 by way of a processor embeds cyclic redundancy check (CRC) bits into a data communication packet representing the input data. The CRC is computed and included in the transmission of each data packet. The cyclic redundancy check is based on an algorithm that computes a checksum for a data stream or packets of any length. These checksums can be used to detect interference or accidental alteration of data during transmission. Cyclic redundancy checks are good at detecting errors caused by electrical or electromagnetic noise and therefore enable robust protection against improper processing of corrupted data encoded in energy streams having communication of instructions and data as a secondary function.

In a step 1506, the external wireless energy source 125 modulates the input data onto a TX (transmit) power signal. For instance, the modulation circuit 127 modulates the power signal as a carrier signal and conveys the input data by adjusting at least one of an amplitude, phase, or frequency of the power signal. In the case of wireless energy transfer by resonant induction, the external wireless energy source 125 can modulate the resonant frequency over a small bandwidth to convey the input data in a power efficient manner. In yet another arrangement, timing intervals between energy emissions can be used to convey input data. In a step 1508, the external wireless energy source 125 transmits the TX power signal to the sensing insert device 100.

In a step 1510, the sensing insert device 100 senses the electromagnetic energy waves on the induction coils. In a step 1512, a RX power signal is generated from the electromagnetic waves. This RX power signal comprises a power signal to provide charge to power to the sensing insert device 100 and a communication signal. As previously discussed in FIG. 14, the compact low-power energy source 1400 by way of the induction coils 1404, rectifier 1406, and regulator 1408 sense and convert electromagnetic waves to a rectified voltage signal that is then used to charge a super capacitor or capacitor. In one configuration, the external wireless energy source 125 and the compact low-power energy source 1400 employ resonant inductive coupling to provide power efficient transmission over short distances (e.g., less than 20 cm). As an example, the inductors (coils) in conjunction with closely spaced capacitor plates are tuned to a mutual resonant frequency to minimize power loss. The external wireless energy source 125 modulates the power signal around the resonant frequency to transmit power efficiently while simultaneously conveying the communication signal.

Returning to FIG. 15, in a step 1514, the sensing insert device 100 demodulates the communication signal from the RX power signal. The demodulation extracts the information or data from the modulated carrier wave. The demodulation circuit can be in one of the rectifier 1406, regulator 1408, power management circuitry 1412, or operational circuitry 1412. In a step 1516, the sensing insert device 100 securely decodes and validates the information or data. In one embodiment, a cyclic redundancy check checksum is performed to verify the data was not corrupted or received incorrectly. The data is forwarded to control and processing circuitry 307. In the example, electronic circuitry 307 is on an ASIC integrated circuit with the communication blocks to perform the demodulation, CRC, encoding/decoding, and data validation. As an example, the circuitry can include envelope detectors, phase detectors, oscillators, multipliers, adders, filters, and logic operators.

The sensing insert device 100 can then proceed to use the decoded down-link data, for example, to control at least one operation, as shown in step 1518. As an example, the control operation can place the sensing insert device 100 in a particular operation mode, such as, stand-by or low-power. As another example, the control operation can download a serial number to a local memory on the sensing insert device 100. The serial number can later be transmitted upon request to a communicatively coupled receiver station 110.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A system to measure a parameter of the muscular-skeletal system including a sensing module having at least one passive sensor therein configured to measure the parameter and having two-way communication capability comprising: a transmitter configured to transmit information via a radio frequency signal; a demodulation circuit, where the demodulation circuit is configured to demodulate a signal; and an induction coil configured to receive a modulated signal on a modulated carrier wave through electromagnetic coupling, where the modulated carrier wave is sent from a wireless energy source, where the demodulation circuit extracts the modulated signal from the modulated carrier wave, where the modulated signal on the carrier wave is produced by a wireless energy source which modulates the power signal to transmit power wirelessly while conveying data by the modulated signal, and where the sensing module, the transmitter, the demodulation circuit and the induction coil are contained within a single unit, where the transmitter is configured to wirelessly send one or more data packets and where each data packet comprises parameter measurements and a priority level, where the transmit information and the receive information are wirelessly sent at different frequencies, where transmit information and receive information are transmitted and received simultaneously, where the sensing module further includes: one or more sensors configured to be coupled to the muscular-skeletal system, where at least one sensor measures load; electronic circuitry operatively coupled to the sensors; and the transmitter coupled to the electronic circuitry for receiving parameter measurements to transmit and where the wireless energy source modulates the power signal about a resonance frequency to transmit power wirelessly while conveying data by the modulated signal, where the sensing module further includes: a rectifier coupled to the induction coil to rectify the signal; a regulator coupled to the rectifier; a capacitor coupled to the regulator where the regulator regulates a voltage on the capacitor; and power management circuitry operatively coupled to the electronic circuitry and the capacitor.

2. The system of claim 1 where the induction coil is configured to charge a capacitor with the carrier wave.

3. The system of claim 2 further including: a rectifier coupled to the induction coil to rectify the electromagnetic signal; a regulator coupled to the rectifier; the capacitor coupled to the regulator where the regulator regulates a voltage on the capacitor; and power management circuitry operatively coupled to the electronic circuitry and the capacitor.

4. The system of claim 1 where an external wireless energy source includes a modulation circuit to couple data or information on the carrier wave and where the external wireless energy source includes at least one data input.

5. The system of claim 1 where the receive information sets a control operation of the sensing module.

6. A method to provide a data downlink to a sensing module, where the sensing module includes a passive sensor, a transmitter and a receiver, where the sensing module is contained within a single unit and where the sensing module is coupled to the muscular-skeletal system, comprising the steps of: modulating input data on a modulated carrier wave of a power signal; transmitting the power signal to the sensing module; sensing the power signal on at least one induction coil in the sensing module; demodulating the input data from the modulated carrier wave of the power signal where the input data is provided to circuitry of the sensing module; charging a power source in the sensing module with the power signal; enabling the sensing module to measure a parameter of the muscular-skeletal system; and measuring the parameter of the muscular-skeletal system where the measurement sensor is within the sensing module, where the transmitter is configured to wirelessly send one or more data packets and where each data packet comprises parameter measurements and a priority level, where the transmit information and the receive information are wirelessly sent at different frequencies, where transmit information and receive information are transmitted and received simultaneously, where the sensing module further includes: one or more sensors configured to be coupled to the muscular-skeletal system, where at least one sensor measures load; electronic circuitry operatively coupled to the sensors; and the transmitter coupled to the electronic circuitry for receiving parameter measurements to transmit and where the wireless energy source modulates the power signal about a resonance frequency to transmit power wirelessly while conveying data by the modulated signal, where the sensing module further includes: a rectifier coupled to the induction coil to rectify the signal; a regulator coupled to the rectifier; a capacitor coupled to the regulator where the regulator regulates a voltage on the capacitor; and power management circuitry operatively coupled to the electronic circuitry and the capacitor.

7. The method of claim 6 further including the steps of: acquiring input data on an external wireless energy source; and encoding input data to include data security.

8. The method of claim 6 further including a step of controlling at least one operation of the sensing module with the input data.

9. The method of claim 8 further a step of transmitting measured parameter data from the sensing module.

10. An insert device for coupling to the muscular-skeletal system comprising: a sensing module configured to measure a parameter of the muscular-skeletal system where the sensing module comprises: a load bearing surface; at least one passive sensor coupled to the load bearing surface, where the sensor measures load; electronic circuitry operatively coupled to the at least one sensor; an induction coil coupled to the electronic circuitry configured to receive a modulated signal on a modulated carrier wave coupled thereto electromagnetically, where the modulated carrier wave is sent from a wireless energy source, where the modulated signal on the modulated carrier wave is produced by a wireless energy source which modulates a power signal to transmit power wirelessly while conveying data by the modulated signal, where the at least one sensor, electronic circuitry, and induction coil are housed in the sensing module, where the sensing module is contained within a single unit, where the transmitter is configured to wirelessly send one or more data packets and where each data packet comprises parameter measurements and a priority level, where the transmit information and the receive information are wirelessly sent at different frequencies, where transmit information and receive information are transmitted and received simultaneously, where the sensing module further includes: one or more sensors configured to be coupled to the muscular-skeletal system, where at least one sensor measures load; electronic circuitry operatively coupled to the sensors; and the transmitter coupled to the electronic circuitry for receiving parameter measurements to transmit and where the wireless enemy source modulates the power signal about a resonance frequency to transmit power wirelessly while conveying data by the modulated signal, where the sensing module further includes: a rectifier coupled to the induction coil to rectify the signal; a regulator coupled to the rectifier; a capacitor coupled to the regulator where the regulator regulates a voltage on the capacitor; and power management circuitry operatively coupled to the electronic circuitry and the capacitor.

11. The insert device of claim 10 where demodulation is used to remove data or information from the modulated carrier wave and where the wireless energy source modulates the power signal about a resonance frequency to transmit power wirelessly while conveying the data or information by the modulated signal.

12. The insert device of claim 11 where a demodulated signal from the induction coil is provided to the electronic circuitry to control at least one operation of the sensing module.

13. The insert device of claim 11 where the electronic circuitry further includes a transmitter configured to receive parameter measurements to transmit and where energy received from the carrier wave charges the capacitor to power the sensing module.

* * * * *